United States Patent
Heller et al.

(10) Patent No.: US 11,123,554 B2
(45) Date of Patent: *Sep. 21, 2021

(54) TARGETED DELIVERY OF MOLECULES USING IMPEDANCE-BASED MONITORING AT ELEVATED TEMPERATURES

(71) Applicant: University of South Florida, Tampa, FL (US)

(72) Inventors: Richard Heller, Tampa, FL (US); Loree C. Heller, Tampa, FL (US); Mark Jeffery Jaroszeski, Wesley Chapel, FL (US)

(73) Assignees: University of South Florida, Tampa, FL (US); Old Dominion University, Norfolk, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/104,833

(22) Filed: Nov. 25, 2020

(65) Prior Publication Data

US 2021/0101003 A1  Apr. 8, 2021

Related U.S. Application Data

(63) Continuation-in-part of application No. 16/999,417, filed on Aug. 21, 2020, now Pat. No. 10,974,045, (Continued)

(51) Int. Cl.
  *A61N 1/32* (2006.01)
  *A61N 5/06* (2006.01)
  *A61F 7/00* (2006.01)

(52) U.S. Cl.
  CPC .............. *A61N 1/327* (2013.01); *A61F 7/007* (2013.01); *A61N 5/0625* (2013.01); *A61F 2007/0071* (2013.01); *A61N 2005/0652* (2013.01)

(58) Field of Classification Search
  CPC .................. A61N 1/327; A61N 5/0625; A61N 2005/0652; A61F 7/007; A61F 2007/0071
  (Continued)

(56) References Cited

U.S. PATENT DOCUMENTS

2005/0096584 A1* 5/2005 Ferek-Petric .......... A61N 1/325
                                                                     604/20
2018/0036529 A1   2/2018 Jaroszeski et al.

OTHER PUBLICATIONS

Atkins, Reginald M. et al. Impedance spectroscopy as an indicator for successful in vivo electric field mediated gene delivery in a murine model. Bioelectrochemistry. Jun. 2017;115:33-40. doi: 10.1016/j.bioelechem.2017.01.004. Epub Jan. 27, 2017. PMID: 28237705.
(Continued)

*Primary Examiner* — Phillip A Gray
(74) *Attorney, Agent, or Firm* — Michele L. Lawson; Smith & Hopen, P.A.

(57) ABSTRACT

A method and system for delivering a molecule to a specific area of a tissue by controlling temperature and impedance is presented. The method is generally comprised of applying heat to a biological structure, such as cells or tissues, to heat the biological structure to a preset temperature after which at least one electroporation pulse is administered to the biological structure. Impedance is measured as a feedback control mechanism after each pulse and pulse parameters are adjusted accordingly until desired impedance is reached. The system generally comprises an electroporation system capable of generating at least one pulse, measuring impedance and measuring temperature. The method may be used to deliver a molecule such as a vaccine or therapeutic to a biological structure, such as for prevention or treatment of SARS-CoV-2 infection.

18 Claims, 11 Drawing Sheets
(5 of 11 Drawing Sheet(s) Filed in Color)

Related U.S. Application Data which is a continuation of application No. 16/813,203, filed on Mar. 9, 2020, now Pat. No. 10,814,129.

(60) Provisional application No. 62/815,708, filed on Mar. 8, 2019.

(58) Field of Classification Search
USPC .......................................................... 604/20
See application file for complete search history.

(56) References Cited

OTHER PUBLICATIONS

Daud, Adil I. et al. Phase I trial of interleukin-12 plasmid electroporation in patients with metastatic melanoma. J Clin Oncol. 2008;26(36):5896-903. Epub Nov. 26, 2008.
Dean, D.A. et al. Electrical Impedance Spectroscopy Study of Biological Tissues. J Electrostat. 2008;66(3-4):165-77. doi: 10.1016/j.elstat.2007.11.005. PubMed PMID: 19255614; PubMed Central PMCID: PMC2597841.
Donate, Amy et al. Application of increased temperature from an exogenous source to enhance gene electrotransfer. Bioelectrochemistry. Jun. 2015;103:120-3. doi: 10.1016/j.bioelechem.2014.08.007. Epub Aug. 23, 2014. PMID: 25193443 DOI: 10.1016/j.bioelechem.2014.08.007.
Ferraro, B. et al. Evaluation of delivery conditions for cutaneous plasmid electrotransfer using a multielectrode array. Gene Ther. May 2011 ; 18(5): 496-500.
Gilbert, Richard et al. Electric field enhanced plasmid delivery to liver hepatocellular carcinomas. Technology in Cancer Research and Treatment, 2002. 1(5):355-363.
Guo, Siqi et al. Electro-gene transfer to skin using a noninvasive multielectrode array. J Control Release. May 10, 2011: 151(3): 256-262.
Guo, Siqi et al. Topical Gene Electrotransfer to the Epidermis of Hairless Guinea Pig by Non-Invasive Multielectrode Array. PLoS One 2013, 8(8): e73423.
Heller, Richard et al. In vivo gene electroinjection and expression in rat liver. FEBS Lett. Jul. 8, 1996;389(3):225-8. PMID: 8766704.
Ivorra, Antoni and Boris Rubinsky. In vivo electrical impedance measurements during and after electroporation of rat liver. Bioelectrochemistry. 2007;70(2):287-95. doi: 10.1016/j.bioelechem. 2006.10.005. PubMed PMID: 17140860.
Matsumoto, T. et al. Successful and optimized in vivo gene transfer to rabbit carotid artery mediated by electronic pulse. Gene Ther. 2001;8(15):1174-9.
Mossop, Brian J. et al. Electric fields in tumors exposed to external voltage sources: implication for electric field-mediated drug and gene delivery. Ann Biomed Eng. 2006;34(10):1564-72. doi: 10.1007/s10439-006-9151-3. PubMed PMID: 16917743.
Neumann, E. et al. Gene transfer into mouse lyoma cells by electroporation in high electric fields. EMBO J. 1982;1(7):841-5.
Zampaglione, Immacolata et al. In vivo DNA gene electro-transfer: a systematic analysis of different electrical parameters. J Gene Med. 2005;7(11):1475-81. doi: 10.1002/jgm.774. PubMed PMID: 15991255.
Granot, Y. et al. In vivo imaging of irreversible electroporation by means of electrical impedance tomography. Phys Med Biol. 2009;54(16):4927-43. doi: 10.1088/0031-9155/54/16/006. PubMed PMID: 19641242.
Ivorra, A. et al. In vivo electrical conductivity measurements during and after tumor electroporation: conductivity changes reflect the treatment outcome. Phys Med Biol. 2009;54(19):5949-63. doi: 10.1088/0031-9155/54/19/019. PubMed PMID: 19759406.
Pliquett, U. and M.R. Prausnitz. Pliquett, U. Electrical Impedance spectroscopy for rapid and noninvasive analysis of skin electroporation. Methods Mol Med. 2000;37:377-406. doi: 10.1385/1-59259-080-2:377.
Grafstrom, G. et al. 99mTc-DTPA uptake and electrical impedance measurements in verification of in vivo electropermeabilization efficiency in rat muscle. Cancer Biother Radiopharm. 2006;21(6):623-35. doi: 10.1089/cbr.2006.21.623. PubMed PMID: 17257078.
Donate, A. et al. Thermal Assisted in Vivo Gene Electrotransfer. Curr Gene Ther. 2016;16(2):83-9. PMID: 27029944 PMCID: PMC5134249.
Titomirov, A.V. et al. In vivo electroporation and stable transformation of skin cells of newborn mice by plasmid DNA. Biochim Biophys Acta. Jan. 17, 1991;1088(1):131-4. PMID: 1703441.
Lambricht, L. et al. Clinical potential of electroporation for gene therapy and DNA vaccine delivery. Expert Opin Drug Deliv. 2016;13(2):295-310. doi: 10.1517/17425247.2016.1121990. Epub Dec. 19, 2015.
Heller, L.C. and Richard Heller. Electroporation gene therapy preclinical and clinical trials for melanoma. Curr Gene Ther. Aug. 2010;10(4):312-7.
Heller, R. et al. Electrically mediated delivery of plasmid DNA to the skin, using a multielectrode array. Hum Gene Ther. 2010;21(3):357-62.
Connolly, R.J. et al. Effectiveness of non-penetrating electroporation applicators to function as impedance spectroscopy electrodes. IEEE Transactions on Dielectrics and Electrical Insulation. 2009;16(5):1348-55.
Broderick K.E. and Laurent M. Humeau. Electroporation-enhanced delivery of nucleic acid vaccines. Expert Rev Vaccines. Feb. 2015;14(2):195-204.
Jiang, S. et al. Neutralizing Antibodies against SARS-CoV-2 and Other Human Coronaviruses. Trends in immunology. 2020;41(5):355-9. Epub Apr. 7, 2020. doi: 10.1016/j.it.2020.03.007. PubMed PMID: 32249063; PMCID: PMC7129017.
Zhou, P. et al. A pneumonia outbreak associated with a new coronavirus of probable bat origin. Nature. 2020;579(7798):270-3. Epub Feb. 6, 2020. doi: 10.1038/s41586-020-2012-7.PubMed PMID: 32015507; PMCID: PMC7095418.
Shi, R. et al. A human neutralizing antibody targets the receptor binding site of SARS-CoV-2. Nature. 2020. Epub May 27, 2020. doi: 10.1038/s41586-020-2381-y. PubMed PMID: 32454512.
Cao, Y. et al. Potent neutralizing antibodies against SARS-CoV-2 identified by highthroughput single-cell sequencing of convalescent patients' B cells. Cell. 2020. Epub May 20, 2020. doi: 10.1016/j.cell.2020.05.025. PubMed PMID: 32425270; PMCID: PMC7231725.
Monteil, V. et al. Inhibition of SARS-CoV-2 Infections in Engineered Human Tissues Using Clinical-Grade Soluble Human ACE2. Cell. 2020;181(4):905-13 e7. Epub Apr. 26, 2020. doi: 10.1016/j.cell.2020.04.004. PubMed PMID: 32333836; PMCID: PMC7181998.
Ciaglia, E. et al. COVID-19 Infection and Circulating ACE2 Levels: Protective Role in Women and Children. Front Pediatr. 2020;8:206. Epub May 12, 2020. doi: 10.3389/fped.2020.00206. PubMed PMID: 32391299; PMCID: PMC7192005.
Pardon, E. et al. A general protocol for the generation of Nanobodies for structural biology. Nature protocols. 2014;9(3):674-93. Epub Mar. 1, 2014. doi: 10.1038/nprot.2014.039. PubMed PMID: 24577359; PMCID: PMC4297639.
Walter, J. et al. Sybodies targeting the SARS-CoV-2 receptor-binding domain. bioRxiv. 2020:2020.04.16.045419. doi: 10.1101/2020.04.16.045419.
Babiuk, S. et al. Electroporation improves the efficacy of DNA vaccines in large animals. Vaccine. 2002;20(27-28):3399-408.
Edelblute, C.M. et al. Controllable Moderate Heating Enhances the Therapeutic Efficacy of Irreversible Electroporation for Pancreatic Cancer. Scientific reports. 2017;7(1):11767. Epub Sep. 20, 2017. doi: 101038/s41598-017-12227-4. PubMed PMID: 28924200; PMCID: PMC5603521.
Edelblute, C.M. et al. Moderate Heat Application Enhances the Efficacy of Nanosecond Pulse Stimulation for the Treatment of Squamous Cell Carcinoma. Technol Cancer Res Treat. 2018;17:1533033818802305. Epub Sep. 27, 2018. doi: 10.1177/1533033818802305. PubMed PMID: 30253713; PMCID: PMC6156209.

\* cited by examiner

FIG. 1A-B

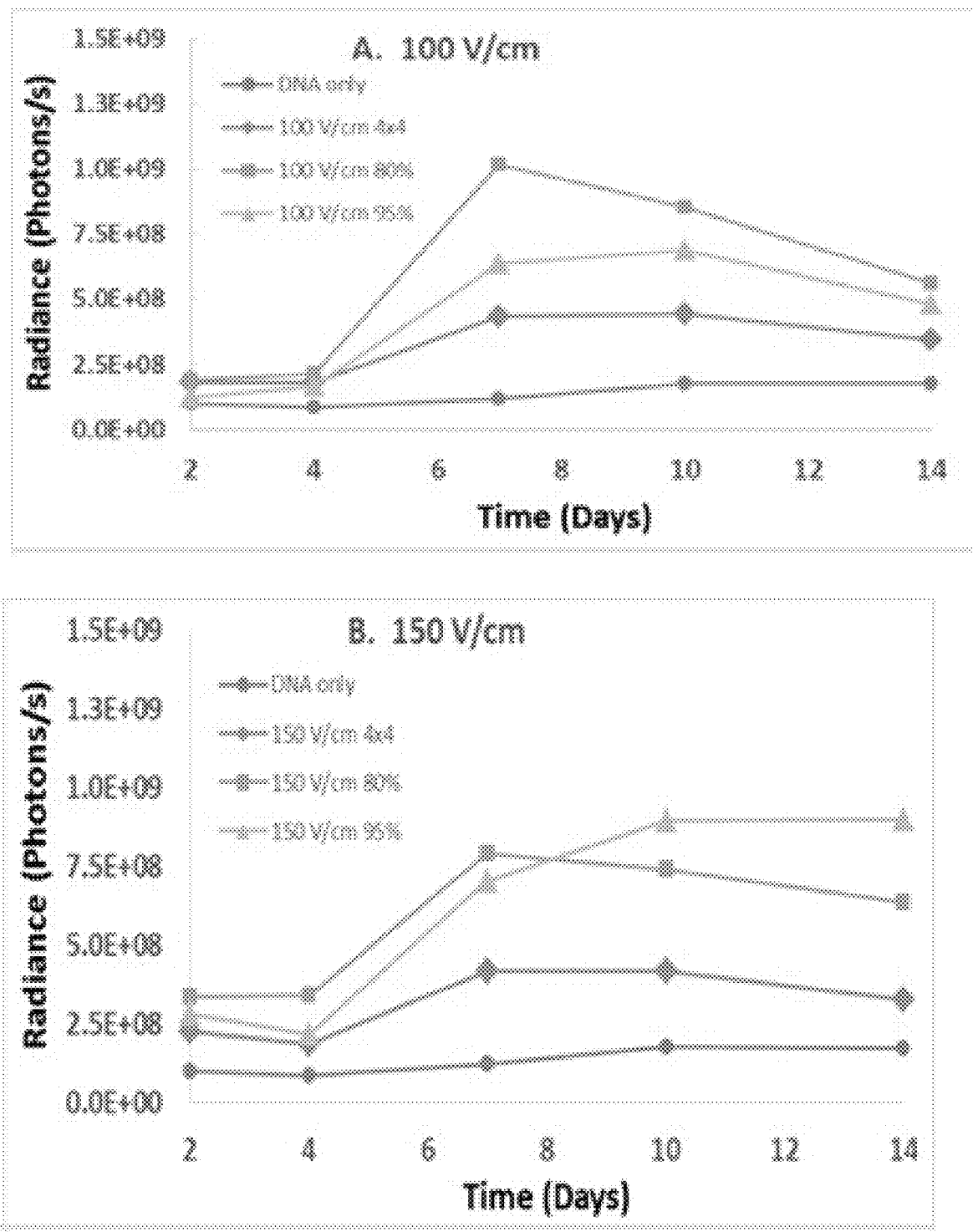
FIG. 8A-B

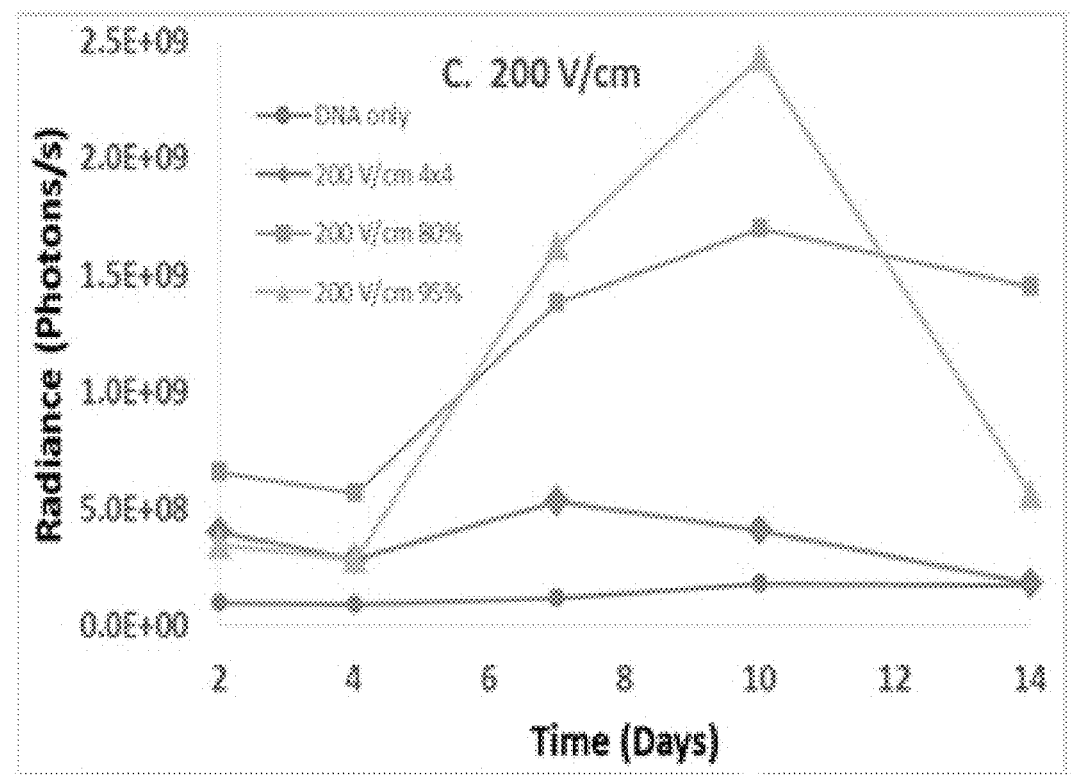
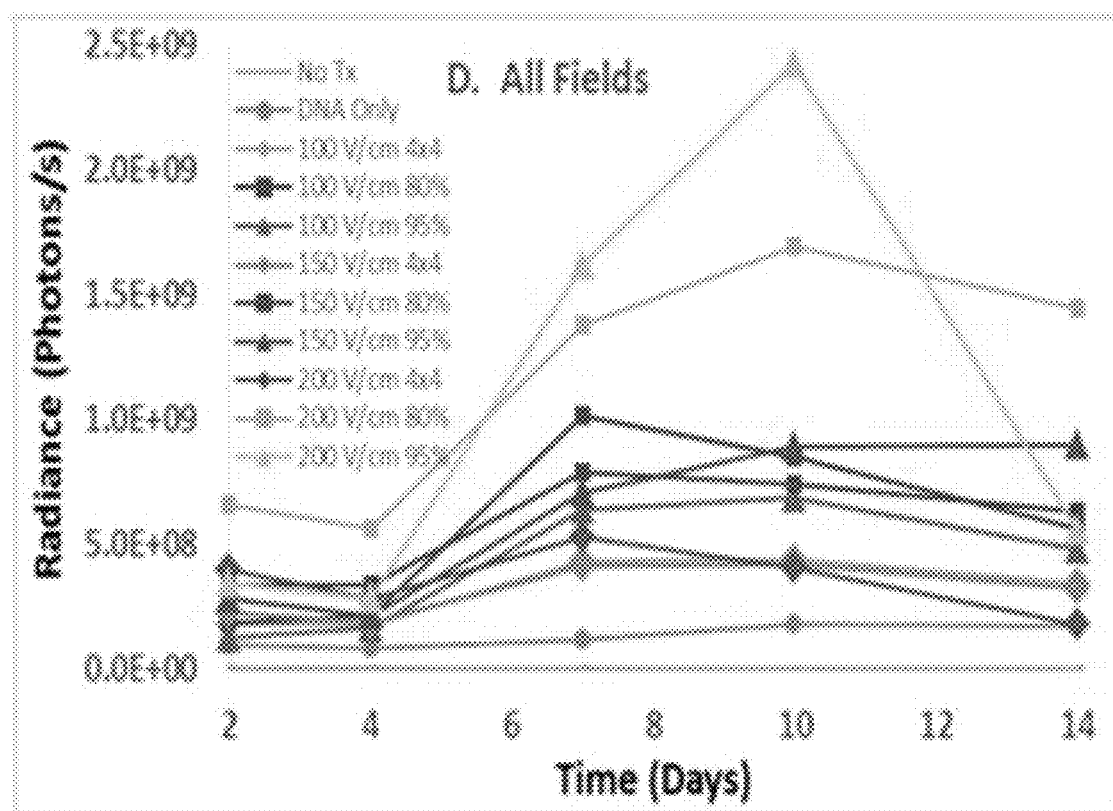
FIG. 8C-D

TARGETED DELIVERY OF MOLECULES USING IMPEDANCE-BASED MONITORING AT ELEVATED TEMPERATURES

CROSS REFERENCE TO RELATED APPLICATIONS

This application is a continuation in part application and claims priority to currently pending U.S. Nonprovisional application Ser. No. 16/999,417, entitled "Targeted Delivery of Molecules Using Impedance-Based Monitoring at Elevated Temperatures", filed Aug. 21, 2020, which is a continuation of and claims priority to U.S. Nonprovisional application Ser. No. 16/813,203, now U.S. Pat. No. 10,814,129, entitled "Targeted Delivery of Molecules Using Impedance-Based Monitoring at Elevated Temperatures", filed Mar. 9, 2020, which is a nonprovisional of and claims priority to U.S. Provisional Application No. 62/815,708 entitled "Targeted Delivery of Molecules Using Impedance-Based Monitoring at Elevated Temperatures", filed Mar. 8, 2019, the contents of each of which are hereby incorporated by reference into this disclosure

GOVERNMENTAL SUPPORT

This invention was made with Government support under Grant Nos. R01EB018956 and R01EB027497 awarded by the National Institute of Biomedical Imaging and Bioengineering (NIBIB). The Government has certain rights in the invention.

FIELD OF INVENTION

This invention relates to targeted delivery of molecules. Specifically, the invention provides a method of targeted delivery of molecules using impedance-based monitoring at elevated temperatures.

BACKGROUND OF THE INVENTION

Of the methods of in vivo gene delivery today, electroporation/electrotransfer has been accepted as having clinical importance/relevance based upon the approximately 100 clinical trials that are in various stages of completion. The majority of these trials were initiated in the past 15 years following the first that was published in 2008.

The accepted mechanism for gene delivery by electroporation (EP) is that direct current (DC) pulses temporarily weaken the barrier properties of cell membranes which ultimately initiates/mediates the entry of exogenous DNA into cells. The method has been used in many tissue types because it is physical in nature and can be tuned to any particular tissue. However, identifying electrical parameters, such as pulse width (micro- to millisecond), amplitude (25-1500 Volts), pulse number (1-100), etc., that result in a desired/optimal biological response, e.g. expression level, immune response, etc., can be a complex process and is analogous to determining the "right" dose of electricity. Furthermore, electrical conditions for delivering DNA to achieve desired expression vary with tissue type.

There are many variables that effect electroporation. These include tissue type, electrode type, subject-to-subject (human or animal) variation, as well as human factors relating to the manual placement of electrodes and the injection of therapeutic molecules. Differences in tissue architecture and/or chemical composition may effectively create unique biological environments from subject to subject that may respond differently to identical electroporation parameters. In order to identify the required electroporation parameters, painstakingly derived empirical electroporation parameters have been the norm for the field since its inception. The derivation of these parameters involves performing multiple series of experiments to investigate the most appropriate electrode to be used to deliver the electric pulses to the subject and the proper applied electric field strength, number of pulses, duration of each pulse, shape of each pulse, and interval between pulses (for multiple pulse protocols). These empirically derived electroporation parameters are what yield the desired biological response for a particular delivery situation, on average. Unfortunately, empirically derived parameters cannot compensate for differences that are encountered when applying the same treatment to multiple different subjects (animals or patients).

Historically, parameters have been determined empirically by first selecting/developing a set of electrodes and subsequently performing multiple experiments that vary one or more of the following parameters: number of pulses applied, electric field intensity, and duration of each pulse. Often, days to months are required before the resulting biological response can be evaluated. Mean data are then used to establish "optimal" electrical treatment parameters for subsequent use in that particular tissue. From a translational perspective, this is concerning as it is critical that each patient receive a correct dose of electricity even though factors can change due to person to person and tissue to tissue variation. Current methods for determining optimal electrical parameters do not and cannot account for this variation. Accordingly, what is needed is a system and method of molecule delivery that accounts for the variability between patients to increase both reliability and control.

SUMMARY OF INVENTION

The inventors have identified two additional physical parameters that markedly increase the success of in vivo gene delivery by electroporation. It was found that modest localized temperature increases in skin (43° C.) during DNA delivery resulted in an 8-fold increase in expression. Further, the temperature increases allowed the magnitude of the applied pulses (voltage/field intensity) to be reduced by about 50% to achieve the same expression when compared to optimal delivery performed at ambient temperature. Similarly, adjusting pulse parameters during electrical treatment based upon real-time tissue impedance measurements resulted in between 6- to 15-fold increases in expression. It was found that pulse magnitudes can be reduced by 50% and still achieve increased expression relative to traditionally optimized conditions. The benefits of manipulating either physical parameter are compelling on their own. However, the combination of localized temperature increases and impedance-based feedback pulsing exhibit at least additive, if not synergistic, effects. The combination treatment provides better control, reduces variation, and further reduces the magnitude of pulses required for delivery.

Currently, delivery of molecules via electrotransfer is done by predetermining the number of pulses, pulse width and amplitude and then using that as a fixed set of parameters for each animal or patient treated. The problem with this approach is that each individual has different tissue properties even if the location between individuals is similar. This is particularly true with respect to the conductance of the tissue and the relative temperature. In addition, within a particular tissue there may also be areas of higher conductance. Therefore, using a standardized approach to pulsing would result in high variability from patient to patient and would also cause uneven distribution of delivery within the tissue.

Controlling process based upon the two physical parameters of temperature and impedance can reduce or virtually eliminate this variability with the tissue and between subjects thus increasing delivery and reproducibility of electroporation-based drug/gene delivery methods thus moving gene therapy closer to recombinant protein drug therapy. In addition, by monitoring both temperature and impedance, one can target the delivery to specific areas within the tissue. Enhancing tissue targeting and controlling dosing by controlling the amount and site of delivery also increases safety and reliability. While the method is described herein as being used on the skin, the method is applicable to any tissue or abnormal growth through the use of catheters, scopes or surgery.

In an embodiment, a method of delivering a molecule to a biological structure of a subject is presented comprising: applying heat to the biological structure to heat the biological structure to a preset temperature; applying at least one electroporation pulse to deliver the molecule into the biological structure; measuring impedance of the biological structure as a feedback control mechanism after each pulse; and adjusting pulse parameters based on the measured impedance of the biological structure until desired impedance is reached indicating delivery of the molecule to the biological structure.

The method may further comprise the steps of injecting a molecule into the biological structure prior to applying heat to the biological structure, measuring impedance prior to applying any pulses to the biological structure, and monitoring the temperature of the biological structure using impedance, thermal imaging, thermistors, thermocouples, thermopiles or combinations thereof. The preset temperature may be at least 35° C. or more specifically, between about 40° C. to about 46° C. In some embodiments, the temperature can be selected from the group consisting of 35° C., 36° C., 37° C., 38° C., 39° C., 40° C., 41° C., 42° C., 43° C., 44° C., 45° C. and 46° C., including all intervening temperatures. The heat applied to the biological structure may be transferred to the tissue by means of a convection, conduction, radiation or combinations thereof.

The pulse parameters may be selected from the group consisting of electric field intensity, pulse duration, pulse polarity, time interval between pulses, and number of pulses administered to the tissue (pulse number). The electric field intensity may be between about 5 V/cm to about 2000 V/cm, including all intervening values. The pulse duration may be between about 1 μs to about 1 second, including all intervening values. The time interval between pulses may be between about 1 μs to about 1 second, including all intervening values. The desired impedance may be at least 10% reduction in impedance as compared to pre-pulse impedance. The impedance feedback may be measured in a range of frequencies from 0 Hz to infinity, preferably between 0 Hz to 4 kHz.

The molecule for delivery may be selected from the group consisting of therapeutic drugs, genes, proteins, nucleic acid sequences, and plasmid DNA.

In another embodiment, a system for the delivery of a molecule into a biological structure is presented comprising: an electroporation device; an electric field generator used to apply pulses to a tissue and coupled to the at least one relay; an impedance measurement system coupled to the at least one relay; and a controller coupled to the at least one relay. The electroporation device is comprised of a handle having proximal and distal ends; an electrode array comprising a plurality of individually addressable electrodes attached at the distal end of the handle; at least one relay for addressing each electrode individually or in combination; at least one heating element disposed within the handle positioned proximal to the electrode array; and a temperature measurement system positioned to measure the temperature of the tissue.

The at least one heating element may be at least one light emitting diode (LED). The at least one heating element may be at least one resistive heating element. The temperature measurement system may be an infrared sensing camera. The impedance measurement system may be a low voltage impedance spectroscope.

In an embodiment, a method of delivering an agent to a biological structure is presented comprising: injecting the agent into the biological structure; heating the biological structure to a preset temperature wherein the biological structure is heated by an element that is separate from electrodes used to apply at least one electroporation pulse; measuring impedance of the biological structure to establish a preset impedance value; applying the at least one electroporation pulse to deliver the molecule into the biological structure; measuring the impedance of the biological structure as a feedback control mechanism after each pulse to determine permeability of cell membranes; and adjusting pulse parameters based on the measured impedance of the biological structure until desired impedance is reached indicating delivery of the molecule to the biological structure; wherein the agent is a vaccine or therapeutic.

The method may further comprise monitoring temperature of the biological structure using impedance, thermal imaging, thermistors, thermocouples, thermopiles or combinations thereof.

The preset temperature may be at least 35° C. or more specifically, between about 40° C. to about 46° C. In some embodiments, the temperature can be selected from the group consisting of 35° C., 36° C., 37° C., 38° C., 39° C., 40° C., 41° C., 42° C., 43° C., 44° C., 45° C. and 46° C., including all intervening temperatures. The heat applied to the biological structure may be transferred to the tissue by means of a convection, conduction, radiation or combinations thereof.

The pulse parameters may be selected from the group consisting of electric field intensity, pulse duration, pulse polarity, time interval between pulses, and number of pulses administered to the tissue (pulse number). The electric field intensity may be between about 5 V/cm to about 2000 V/cm, including all intervening values. The pulse duration may be between about 1 μs to about 1 second, including all intervening values. The time interval between pulses may be between about 1 μs to about 1 second, including all intervening values. The desired impedance may be at least 10% reduction in impedance as compared to pre-pulse impedance. The impedance feedback may be measured in a range of frequencies from 0 Hz to infinity, preferably between 0 Hz to 4 kHz.

The agent being delivered by the method may be a SARS-CoV-2 vector comprising: a transcription initiation sequence; a nucleic acid sequence encoding a SARS-CoV-2 spike protein, domains of the SARS-CoV-2 spike protein, or homologous sequences thereof; and a secretion sequence.

Alternatively, the SARS-CoV-2 vector may comprise: a transcription initiation sequence; a nucleic acid sequence encoding a soluble form of an ACE2 extracellular domain or a homologous sequence thereof; and a secretion sequence.

Alternatively, the SARS-CoV-2 vector may comprise: a transcription initiation sequence; a nucleic acid sequence encoding at least one nanobody that binds specific epitopes of a SARS-CoV-2 spike protein or a homologous sequence thereof; and a secretion sequence.

In an embodiment, a method of determining successful delivery of an agent to a biological structure is presented comprising: delivering the agent to the biological structure; measuring the impedance of the biological structure as a feedback control mechanism after injection of the agent into the biological structure to determine a preset impedance value and after each pulse to determine permeability of cell membranes; and adjusting pulse parameters based on the measured impedance of the biological structure until desired impedance is reached indicating successful delivery of the molecule to the biological structure.

Delivery of the agent to the biological structure comprises injecting the agent into the biological structure; heating the biological structure to a preset temperature wherein the biological structure is heated by an element that is separate from electrodes used to apply at least one electroporation pulse; and applying the at least one electroporation pulse to deliver the molecule into the biological structure.

The agent may be a vaccine or therapeutic such as a SARS-CoV-2 vector.

The preset temperature may be at least 35° C. or more specifically, between about 40° C. to about 46° C. In some embodiments, the temperature can be selected from the group consisting of 35° C., 36° C., 37° C., 38° C., 39° C., 40° C., 41° C., 42° C., 43° C., 44° C., 45° C. and 46° C., including all intervening temperatures. The heat applied to the biological structure may be transferred to the tissue by means of a convection, conduction, radiation or combinations thereof. The temperature of the biological structure may be monitored.

The pulse parameters may be selected from the group consisting of electric field intensity, pulse duration, pulse polarity, time interval between pulses, and number of pulses administered to the tissue (pulse number). The electric field intensity may be between about 5 V/cm to about 2000 V/cm, including all intervening values. The pulse duration may be between about 1 µs to about 1 second, including all intervening values. The time interval between pulses may be between about 1 µs to about 1 second, including all intervening values. The desired impedance may be at least 10% reduction in impedance as compared to pre-pulse impedance. The impedance feedback may be measured in a range of frequencies from 0 Hz to infinity, preferably between 0 Hz to 4 kHz.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a fuller understanding of the invention, reference should be made to the following detailed description, taken in connection with the accompanying drawings, in which:

FIG. 8A-B are a series of images depicting radiance/luciferase following delivery with a feedback controlled system. Luciferase encoding plasmid was delivered by electroporation using (A) 100 V/cm pulses standard 4×4 pulses and by impedance feedback to reduce impedance by 80% and 95%; (B) 150V/cm electric pulses for the same treatment groups as in (A).

FIG. 8C-D are a series of images depicting radiance/luciferase following delivery with a feedback controlled system. Luciferase encoding plasmid was delivered by electroporation using (C) 200 V/cm pulses for the same treatment groups as in (A) and (B); (D) combination of data from A, B and C.

DETAILED DESCRIPTION OF THE PREFERRED EMBODIMENT

Figure 1:
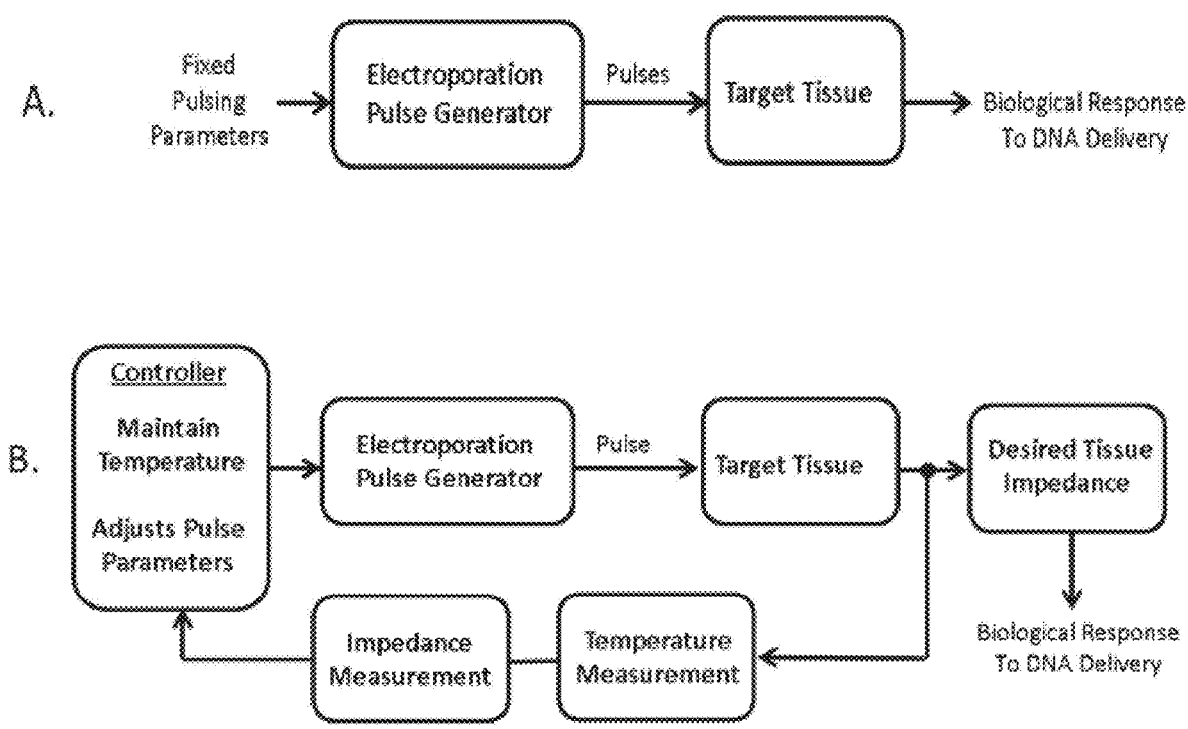
FIG. 1A-B is a diagram of an (A) open-loop control system (prior art) and (B) closed-loop feedback control system for electroporative DNA delivery.

In the following detailed description of the preferred embodiments, reference is made to the accompanying drawings, which form a part hereof, and within which are shown by way of illustration specific embodiments by which the invention may be practiced. It is to be understood that other embodiments may be utilized, and structural changes may be made without departing from the scope of the invention.

Definitions

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supersedes any disclosure of an incorporated publication to the extent there is a contradiction.

All numerical designations, such as temperature, time, and concentration, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

Numerical data may be expressed or presented herein in a range format. Where a range of values is provided, it is understood that each intervening value, to the tenth of the unit of the lower limit, unless the context clearly dictates otherwise, between the upper and lower limits of that range is also specifically disclosed. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose, such as a pharmaceutical formulation. As used herein the term "about" refers to ±10% of the numerical.

As used in the specification and claims, the singular form "a", "an" and "the" include plural references unless the context clearly dictates otherwise.

As used herein, the term "comprising" is intended to mean that the products, compositions and methods include the referenced components or steps, but not excluding others. "Consisting essentially of" when used to define products, compositions and methods, shall mean excluding other components or steps of any essential significance. "Consisting of" shall mean excluding more than trace elements of other components or steps.

It may be appreciated by one of skill in the art that biological cells exist in many forms and in many types. In mammals, for example, there exist four basic types of cells: cells of epithelial, connective, muscle, and nervous tissue. The term "cell", however, is to be broadly interpreted and the devices and methods described herein apply to all types of living cells including prokaryotes, eukaryotes and plant cells. In addition, the term "cell" also includes artificial cells such as liposomes and micelles. The term "cell" also has additional meaning which encompasses a single cell, cells in culture, cell aggregates, and a cell that is part of a tissue. Moreover, the term "cell" can also include a cell structure such as an inter-membrane space, organelle or sub-cellular compartment. Cells may be in vivo or in vitro.

The term "tissue" refers to a complex material which may include several types of cells. An illustrative tissue includes skin, including the epidermis (including the stratum corneum, lucidum, granulosum, spinosum and germinativum), dermis and/or hypodermis. Other tissues to which this method may be applied include, but are not intended to be limited to, tumor, skeletal muscle, smooth muscle, blood, blood vessel, brain, lymph, liver, pancreas, kidney, bone, colon, small intestine, cardiac, lung, breast, testes, prostate, and cornea. In a specific example, the present invention can be used for the transdermal delivery of a target molecule.

The term "biological structure" refers to any cell, group of cells, extracellular matrix, tissue, organ and/or tissue structure, whether in vivo or in vitro.

The term "molecule", as used herein, refers to any type of molecular species. The devices and methods described herein are particularly applicable to therapeutic drugs, genes, proteins, nucleic acid sequences, and plasmid DNA but can be applied to any type of molecule. In addition, the devices and methods are applicable for simultaneously affecting more than one type of molecule. Furthermore, the manipulation of these molecules and biological structures can be for the purposes of the enhancement of therapeutic molecule efficacy for the treatment of a disease or wound or for the prevention of a disease as in a vaccine.

The term "skin" as used herein refers to each of the layers of the skin including the epidermis, stratum corneum, stratum lucidium, stratum granulosum, stratum spinosum, and stratum basale. Molecules delivered by the present invention can be applied to the epidermis and travel through any or all layers of the skin to be delivered into the systemic circulation or delivered to one or more living cells in the skin or deeper tissues in the body.

The devices and methods described herein can be applied to any biological structure; either in vivo or in vitro. The devices and methods described herein can be used for diagnostic and/or molecular identification purposes; research purposes; wound healing purposes; and treating or preventing disease.

"Impedance" as used herein refers to the opposition of an electric current to the flow of an alternating or direct current of a single frequency equal to the square root of the sum of the squares of the resistance and the reactance, expressed in ohms. Impedance may be measured at any frequency from 0 Hz to infinity. In some embodiments, impedance feedback is measured at any frequency below 4 kHz. In another embodiment, impedance feedback is measured between about 0 Hz to about 4 kHz.

"Pulse" or "pulsation" as used herein refers to a change in voltage or current intensity that lasts for a short duration of time. The duration of the pulses used herein last between about 1 μs to about 1 second. Examples of pulse polarity include unipolar and bipolar pulses. "4×4 pulsing" refers to two sets of four pulses being applied normal (90 degrees) to each other. For example, using 4 electrodes arranged in a square geometry, a first set of four pulses may be applied with electrodes 1 and 4 as positive and electrodes 2 and 3 negative. After a given time interval, a second set of four pulses in which electrodes 1 and 2 are positive and 3 and 4 are negative is applied. 4×4 pulsing can also be applied to multi-electrode arrays in which two sets of four pulses are applied in each sector in series. "2×2 pulsing" is similar except two pulses are applied in each direction. "Pulse number" as used herein refers to the number of pulses administered to the biological structure. The electric pulse may be rectangular, exponentially decaying, of any shape or combinations thereof. The pulse may be direct current, alternating current or combinations thereof.

"Electroporation" as used herein refers to the application of an electrical field to a biological structure, such as a cell or tissue, to increase the permeability of the cell membrane to allow molecules to be introduced to the cell.

"Electrotransfer" as used herein refers to the use of an electric field, such as through electroporation, to transfer molecules such as drugs or genetic material into cells, tissues, or other biological structures.

"Heating" or "applying heat" as used herein refers to the process in which the temperature of a biological structure is increased. Heating may be accomplished by any convective, conductive, or radiative means, including combinations thereof, known to those of skill in the art. Exemplary heating methods include, but are not limited to, application of warm air, contact with a warm surface, infrared radiation (IR), electromagnetic waves or emissions at any frequency, microwave emissions, chemical means such as chemical containing heat pads, and combinations thereof.

"Heating element" or "heat generation device" or "element" as used herein refers to any device capable of converting energy to heat. Exemplary heating elements include, but are not limited to, light emitting diodes (LEDs); chemical containing heat pads; electromagnetic wave generators; optic fibers connected to an infrared laser source; resistive heating elements composed of metallic alloys, ceramic materials or ceramic metals; and combinations thereof.

"Temperature measurement device" as used herein refers to any device capable of directly or indirectly measuring the temperature of a biological structure. Examples of temperature measurement devices include, but are not limited to, thermocouples, thermopiles, thermistors, infrared (IR) sensors, heat sensing cameras including infrared (IR) sensing cameras, impedance measurement devices, and combinations thereof.

"Temperature monitoring" as used herein refers to the process of directly or indirectly measuring the temperature of a biological structure over a period of time. Exemplary methods for temperature monitoring include, but are not limited to, impedance measurement; thermal imaging; temperature measurement devices such as thermistors, thermocouples, thermopiles, or any other temperature measurement device that directly or indirectly measures temperature or correlates temperature to a variable.

"Relay" as used herein refers to any device, switch, or means that can be used to address an electrode. Generally, the relay is activated by a current or signal in one circuit to open or close another circuit.

"Infection" as used herein refers to the invasion of one or more microorganisms such as bacteria, viruses, fungi, yeast, or parasites in the body of a patient in which they are not normally present. In certain embodiments, the infection is from a respiratory virus such as SARS-CoV-2 (COVID-19).

"Vaccine" as used herein refers to an antigenic composition usually comprising an infectious factor or a portion of an infectious factor, such as an antigen, administered into the body to elicit an immune response. The vaccine may also be comprised of an immune adjuvant in some embodiments. The antigenic portion may be a microorganism such as a virus or bacterium; a natural product purified from a microorganism; or a synthetic or genetically engineered protein, peptide, polysaccharide, or similar product.

The vaccine compositions of the present invention may be formulated according to known methods, e.g. as nucleic acid vaccines such as DNA and RNA vaccines, transdermal vaccines, topical vaccines, and as combination vaccines. The dosages may be selected by standard processes as known by those of ordinary skill in the art. For vaccines which are improvements on known vaccines, a lower dosage than the known vaccine dosage is possible for the same protection and is therefore preferred. The vaccine may be provided in a storage stable form such as being lyophilized, optionally being provided in combination with a suitable reconstitution solution. In an embodiment, the vaccine is a plasmid-based DNA vaccine. In some embodiments, the vaccine is a SARS-CoV-2 vector that is a plasmid containing a nucleic acid sequence encoding the SARS-CoV-2 spike protein, domains of the SARS-CoV-2 spike protein or homologous sequences thereof.

"Therapeutic" or "therapeutic agent" as used herein refers to a compound or composition that induces a desired pharmacological and/or physiological effect on a subject when administered in a therapeutically effective amount. In some embodiments, the therapeutic is used to treat a viral infection. In some embodiments, the viral infection is a SARS-CoV-2 infection. In some embodiments, the therapeutic is a SARS-CoV-2 vector that is a plasmid containing a nucleic acid sequence encoding the SARS-CoV-2 spike protein, a nucleic acid sequence encoding a soluble form of the ACE2 extracellular domain, or a nucleic acid sequence encoding one or more nanobodies that bind specific epitopes of the SARS-CoV-2 spike protein.

"Nanobody" as used herein refers to a single domain antibody capable of selectively binding to a specific antigen. In some embodiments, the nanobody may bind specific epitopes of the SARS-CoV-2 spike protein. In some embodiments, the nucleic acid sequence of the nanobody may be incorporated into a plasmid for use as a vaccine or therapeutic for SARS-CoV-2 infection.

"Agent" or "active agent" as used herein refers to a composition, compound, chemical, extract or substance that has measurable specified or selected physiologic activity when administered to a subject in a therapeutically effective amount. In some embodiments, the agent is a therapeutic or vaccine. In some embodiments, the therapeutic or vaccine is in the form of a vector. In some embodiments, the vector is a plasmid encoding the SARS-CoV-2 spike protein or domains of the spike protein, a nucleic acid sequence encoding a soluble form of the ACE2 extracellular domain, a nucleic acid sequence encoding one or more nanobodies that bind specific epitopes of the SARS-CoV-2 spike protein or homologous sequences thereof. In some embodiments, the agent may be a therapeutic agent such as a SARS-CoV-2 vector capable of treatment of a viral infection such as SARS-CoV-2. In other embodiments, the agent may be a vaccine such as a SARS-CoV-2 vector capable of preventing a viral infection such as SARS-CoV-2.

"Subject" as used herein refers to an animal, preferably a mammal, more preferably a human, to whom treatment is administered, including prophylactic treatment with the compositions of the present invention. The terms "subject" and "patient" are used interchangeably herein.

"Therapeutically effective amount" as used herein refers to that amount of a therapy (e.g., a therapeutic agent or vaccine) sufficient to result in the amelioration of a viral, bacterial, or fungal infection or one or more symptoms thereof, prevent advancement of a viral, bacterial or fungal infection, or cause regression of a viral, bacterial or fungal infection. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration. The therapeutically effective amount is determined based on such considerations as known in the art including the recipient of the treatment, the recipient's tolerance for the compound, the disorder being treated, the severity of the disorder being treated, the composition containing the compound, the time of administration, the route of administration, the duration of treatment, the potency of the compound, the bioavailability of the compound, the rate of clearance of the compound from the body, and whether or not another active agent is co-administered.

The dosing of compounds and compositions of the present invention to obtain a therapeutic or prophylactic effect is determined by the circumstances of the patient, as known in the art. The dose administered may vary with the particular composition, the method of administration, and the particular disorder being treated. The dosing of a patient herein may be accomplished through individual or unit doses of the compounds or compositions herein or in combination with or concurrently with one or more other therapeutics for the indicated disorder.

"Administration" or "administering" is used to describe the process in which compounds of the present invention, alone or in combination with other compounds, are delivered to a patient. The composition or compounds may be administered in various ways including, but not limited to, injection followed by electroporation using heat and impedance. Each of these conditions may be readily treated using other administration routes of compositions of the present invention to treat a disease or condition. The compositions used in the present invention may be administered individually, or in combination with or concurrently with one or more other therapeutics for viral, bacterial or fungal infection, specifically SARS-CoV-2 infection.

"Treatment" or "treating" as used herein refers to any of: the alleviation, amelioration, elimination and/or stabilization of a symptom, as well as delay in progression of a symptom of a particular disorder. For example, "treatment" of a viral, bacterial or fungal infection may include any one or more of the following: amelioration and/or elimination of one or more symptoms associated with the viral, bacterial or fungal infection, reduction of one or more symptoms of the viral, bacterial or fungal infection, stabilization of symptoms of the viral, bacterial or fungal infection, and delay in progression of one or more symptoms of the viral, bacterial or fungal infection.

"Prevention" or "preventing" as used herein refers to any of: halting the effects of the viral, bacterial or fungal infection, reducing the effects of the viral, bacterial or fungal infection, reducing the incidence of the viral, bacterial or fungal infection, reducing the development of the viral, bacterial or fungal infection, delaying the onset of symptoms of the viral, bacterial or fungal infection, increasing the time to onset of symptoms of the viral, bacterial or fungal infection, and reducing the risk of development of the viral, bacterial or fungal infection.

The term "normal" or "control" as used herein refers to a sample or cells or patient which are assessed as not having a viral, bacterial or fungal infection.

"Homology" or "homologous" or "substantially similar" as used herein refers to a nucleic acid sequence which retains the function of such nucleic acid sequence but which differs from such nucleic acid sequence by the addition, deletion, mutation, and/or substitution of one or more nucleotides. Nucleotide sequences are substantially similar to another nucleic acid sequence if these percentages are from 100% to 80%, including all percentages in between. For example, "homologous" includes a nucleotide sequence possessing at least 80% sequence identity, at least 81% sequence identity, at least 82% sequence identity, at least 83% sequence identity, at least 84% sequence identity, at least 85% sequence identity, at least 86% sequence identity, at least 87% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to the target sequence, including all percentages in between to the hundredth of a percent.

The term "nucleic acid" as used herein refers to the repetition of monomers (nucleotides) that are bound by phosphodiester bonds. The two main classes of nucleic acids are deoxyribonucleic acid (DNA) and ribonucleic acid (RNA). In some embodiments, the nucleic acid used is DNA.

The term "vector" as used herein refers to a plasmid or viral chromosome containing a fragment of foreign nucleic acid sequence such as a DNA or RNA sequence. The vector is used to introduce this foreign nucleic acid sequence into a host cell. Any vector is contemplated for use with the invention. In some embodiments, the vector is a plasmid. In some embodiments, the plasmid is a SARS-CoV-2 vector. The SARS-CoV-2 vector may be a plasmid containing a transcription initiation sequence, a secretion sequence and a nucleic acid sequence encoding the SARS-CoV-2 spike protein, a nucleic acid sequence encoding a soluble form of the ACE2 extracellular domain, or a nucleic acid sequence encoding a nanobody that binds specific epitopes of the SARS-CoV-2 spike protein. The list is exemplary and other SARS-CoV-2 vectors containing different nucleic acid sequences or homologous nucleic acid sequences to those described above are contemplated. While a SARS-CoV-2 vector is used in some embodiments, these are exemplary and vectors drawn towards treating or preventing any infection are contemplated.

The inventors have incorporated concepts that are practiced in controls engineering to modulate two new variables, temperature and impedance, the monitoring and manipulation of which have been shown to enhance delivery of molecules such as DNA via electroporation in vivo. FIG. 1A shows the open loop system of the current state of the art which exemplifies the lack of control in the process of applying electroporation in vivo. In the procedure, a fixed set of pulses, having fixed pulse parameters, are applied at ambient tissue temperature with no attempt being made to control the temperature or customize pulsation. In contrast, FIG. 1B illustrates the instantly claimed closed loop system in which the temperature of the local tissue (skin) area is increased and maintained at a constant preset temperature with impedance spectroscopy being used to measure the resulting tissue condition after every electroporation pulse. Adjustments can be made after measurement of the tissue condition by applying an additional pulse or stopping pulsing.

The hardware required for temperature control and impedance measurement is capable of being adapted to current electroporation systems as such systems all have electrodes that are in contact with the target tissue during treatment. While electrode arrangement can differ between devices, current devices can be adapted to a preferred electrode arrangement to allow for temperature increases and impedance feedback. For example, the inventors have found that an electrode arrangement of four electrodes may be used in some applications. In some embodiments, a multi-electrode array (MEA) may be used which may be comprised of nine subsets of four electrodes with each set of four electrodes comprising a sector within the overall array. In some embodiments, an optical fiber located within each sector for infrared emission to provide focused tissue heating. In other embodiments, heating elements and temperature measurement devices are disposed within the electroporation device. While these electrode arrangements are exemplary, any arrangement that allows for temperature increases and impedance feedback may be used. Alternatively, the heating and control systems may be added to existing electrode and pulse generators with some adaptation using electrically actuated switches or relays.

Example 1—Increasing Temperature Increases Expression

Temperature increases have been shown to enhance delivery by affecting membrane permeability in vitro during electroporation; temperature reductions to 4° C. resulted in reduced delivery [Kanducer, M, et al, Bioelectrochemistry 2008]. Hyperthermia has been shown to increase the delivery of chemotherapeutics. [Ponce A M, et al, In J Hypertherm, 2006, May, J P, et al Exp Opinion in Drug Delivery, 2013, Pace, M, et al, J. Exp Clin Cancer Res, 2005, Sarnaik, A A, et al, Recent Results Cancer Research, 2007] Furthermore, local heating of tissues increases vasodilation with maximum blood flow being achieved at 42° C. in skin. The effects are maintained for up to an hour after heating [Taylor, W F, et al, J. Appl Physiol, Respir Environ, Exerc Physiol, 1984, Kellogg, D L, J Appl Physiol, 2006]. Temperature should affect gene delivery by electroporation in vivo as the accepted mechanism is that the DC pulses temporarily weaken the barrier properties of cell membranes which ultimately initiates/mediates the entry of plasmid DNA into cells. The inventors show that influencing these barrier properties before pulsation can improve delivery and/or require lower energy DC pulses.

Experiments to determine if moderate temperature increases could improve DNA delivery in vivo via electroporation were previously conducted by the inventors in Hartley guinea pig skin by delivering DNA encoding luciferase using an electroporation device comprised of four surface electrodes spaced 5 mm apart and arranged in a square pattern. The electrodes protruded about 5 mm from the distal end of the handle and an output from an infrared laser, flush with the distal end of the handle, was positioned between the electrodes to provide IR heat. (Donate A, Bulysheva A, Edelblute C, Jung D, Malik M A, Guo S, Burcus N, Schoenbach K, Heller R. Thermal Assisted In Vivo Gene Electrotransfer. Curr Gene Ther. 2016; 16(2):83-9)

Laser output was adjusted to heat the skin to an optimal temperature of 43° C. in about 30 seconds. Timing was predetermined using a thermocouple positioned under the guinea pig skin. The guinea pig skin was injected intradermally with 100 µg DNA in 50 µl of saline after which the electrode was placed in contact with the guinea pig skin to heat the tissue. A set of four 150 ms pulses were applied using a commercial pulse generator with electrode numbers 1 and 4 used as positive and electrode numbers 2 and 3 used as negative. There was a 150 ms time gap between pulses. With the aid of a mechanical switch, another set of 4 pulses was applied using electrodes 1 and 2 as positive and electrodes 3 and 4 as negative. This type of pulsing has been termed 4×4 due to the two sets of 4 pulses being applied normal to each other. (Donate et al. 2016)

It was found that preheating the tissue at both voltages increased the peak luciferase levels by about 4- to 8-fold relative to electroporation without heat. Further, preheating and subsequently pulsing with 50V yielded an almost identical expression profile as compared to 100V with no preheating. Thus, it was found that heating increased expression and allowed the use of 50% less voltage. (Donate et al. 2016)

Multi-Electrode Array

Figure 2:
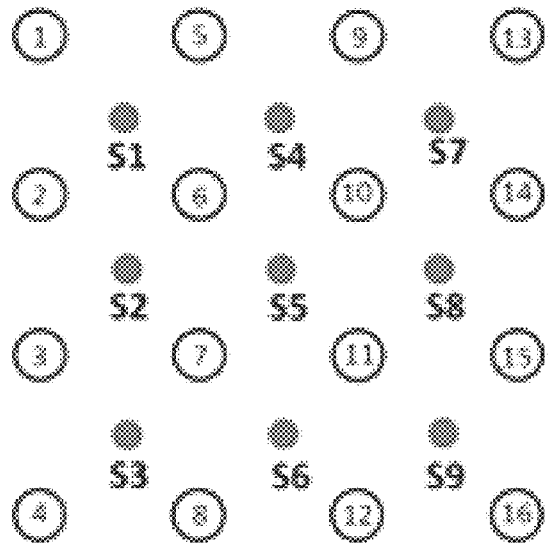
FIG. 2 is an image of the electrode configuration of the 16 multi-electrode array (16 MEA). Sixteen individually addressable electrodes (numbered 1-16) are shown a configured into 9 sections (S1-S9), with each section comprising 4 electrodes. Solid dots are representative of optical fibers.

The inventors previously developed a multi-electrode array (MEA) incorporating an IR heat source and having more closely spaced electrodes than those by Donate et al., incorporated herein by reference. Closely spaced electrodes allow for the application of lower voltages since the electric field intensity is scaled by the distance between the electrodes. The applicator array was comprised of 16 gold plated electrodes that were 0.5 mm in diameter with rounded ends. The electrodes were spaced 2.5 mm apart, center to center and this configuration was termed a multi-electrode array (MEA) with 16 electrodes (16 MEA). FIG. 2 illustrates an exemplary MEA having nine subsets of four electrodes with each set of four electrodes comprising a sector (labeled S1-S9) within the overall array. An optic fiber is located in each sector for IR emission to provide tissue heating (shown as the nine solid dots in FIG. 2). Heat was provided by an infrared laser source that was channeled to each of the nine optical fibers in order to uniformly heat the treatment area.

Method

The tissue was preheated for about 25 seconds until it reached 43° C. prior to any pulses being administered. Pulses were subsequently administered to the electrode in a particular manner to uniformly treat the 8×8 mm area covered by the electrode. For example, the first sector is comprised of electrodes 1, 2, 5, and 6 (FIG. 2, upper left corner, S1). Four pulses were applied using electrodes 1 and 2 as positive with 5 and 6 as negative. Afterward, four pulses were applied normal (90 degrees) to the first four by making 1 and 5 positive with 2 and 6 negative which completed the pulsing of the first sector. Pulses were then applied to the second sector comprised of pins 2, 3, 6, and 7 in an analogous manner. Pulses were applied to each sector in series until the 9th and final sector. This is similar to the 4×4 pulsing described in Example 2 but applied 9 times in series. 2×2 pulsing has also been used. 2×2 pulsing is similar to 4×4 pulsing except that 2 pulses are applied in each direction for each sector.

Figure 3:
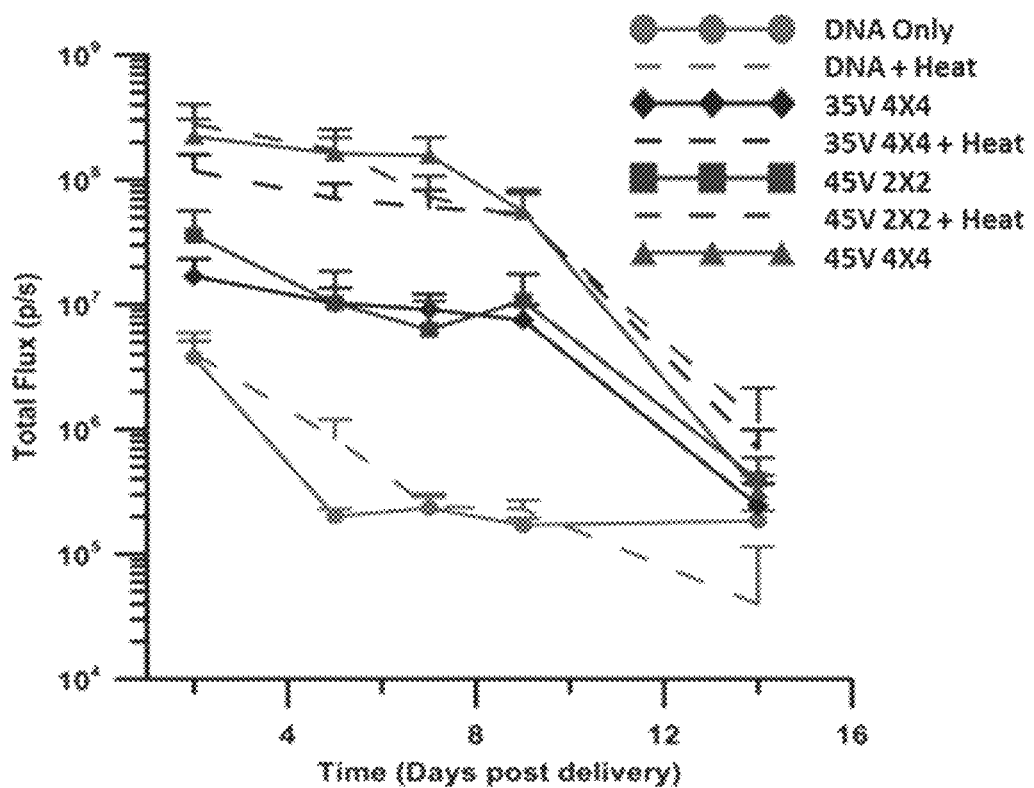
FIG. 3 is a graph depicting luciferase levels in guinea pig skin after thermally assisted in vivo delivery by electroporation using the modified 16 MEA to preheat tissue to 43° C. N=8 individual treatment sites, bars are standard deviation.

FIG. 3 shows the influence of heating the skin prior to delivery using a 16 pin multi-electrode array (MEA) that contained 9 optical fibers for IR heating. Basic testing showed that it provided more uniform heating and allowed lower absolute voltages to be utilized as compared to the previous electrode described above. This latter point makes treatment more comfortable for patients and may be low enough that local/general anesthesia is not required. The figure shows data from animals that were treated using 45V pulses in a 4×4 manner which were optimized parameters (for max expression) with no heat applied. Transient and mild superficial burns (resolved in 48-72 hours) resulted from these optimal conditions. Applying pulses with the same voltage (45 V) in a 2×2 (half the number of pulses as 4×4) manner after preheating resulted in an identical luciferase profile with no adverse tissue effects, thus, preheating can reduce the number of pulses required. Furthermore, preheating and then applying lower voltage pulses (35V) in a 4×4 manner again resulted in a gene expression profile that was identical to the unheated 45V pulsed group. Thus, preheating allowed a ~25% reduction in applied voltage with no adverse tissue effects. In addition, comparing like treated groups except for the use of heat revealed that peak luciferase levels were increased about 8-fold due to heating. Thus, it is becoming clear that preheating the tissue is one physical parameter that can be used to increase delivery/expression, reduce the applied voltage, reduce the number of applied pulses, and avoid adverse tissue effects.

Figure 4:
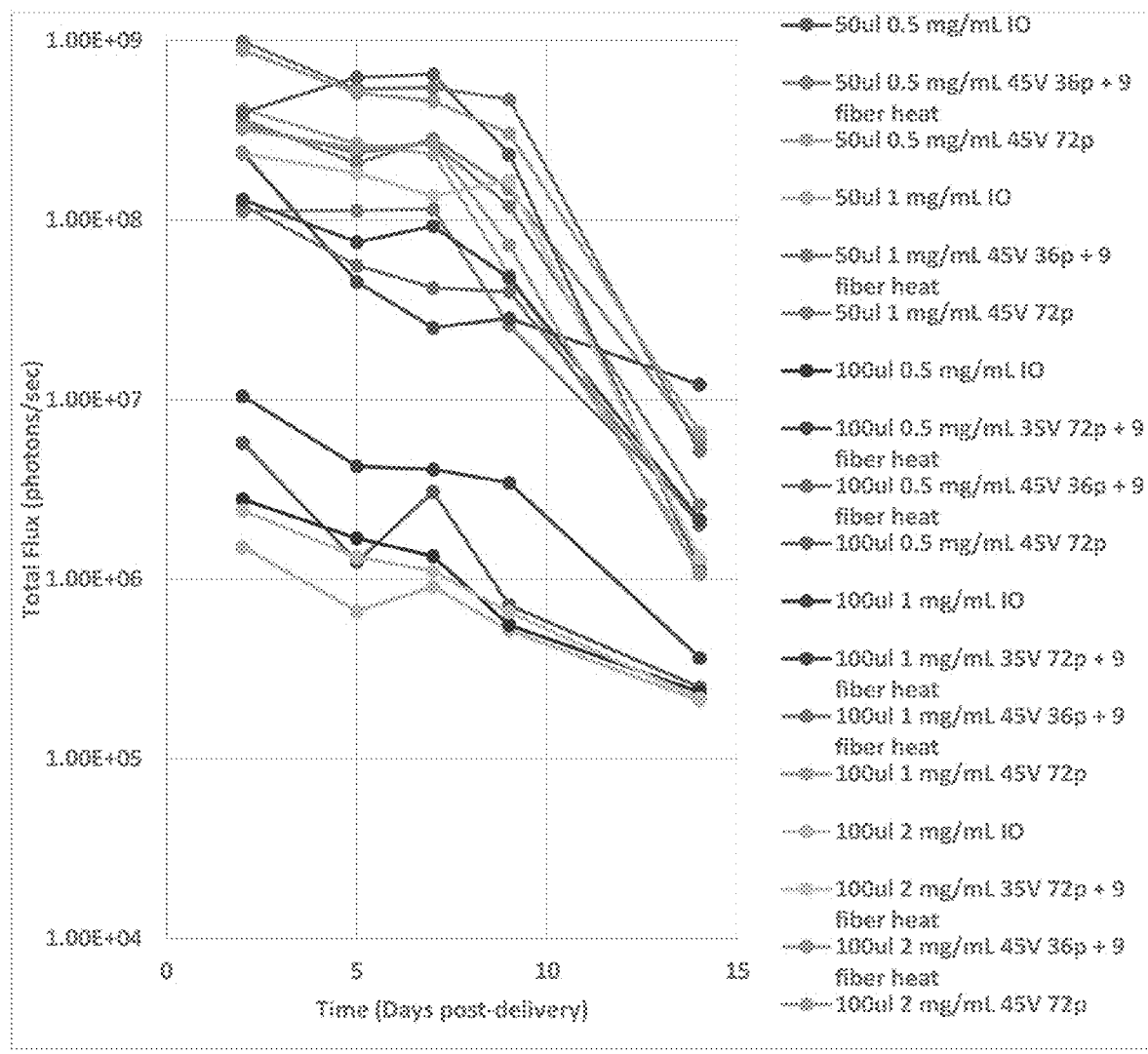
FIG. 4 is a graph depicting an evaluation of volume and plasmid concentration. The groups tested were as follows: 45V pulses in a 4×4 manner with no heat applied and 72 pulses; 45 V in a 2×2 with heat and 36 pulses applied; 35V pulses in a 4×4 manner with heat and 72 pulses; and injection only without pulses. For each delivery condition (group), DNA was injected at 50 µl or 100 µl at a concentration of 0.5, 1.0 or 2.0 mg/ml. The best results were obtained utilizing a 100 µl injection volume at a concentration of 1.0 mg/ml.

A modified 16 MEA containing 9 optical fibers for IR heating and temperature control was tested to evaluate the influence of injection volume and concentration of plasmid DNA. Previous experiments demonstrated that the MEA with 9 fibers provided more uniform heating and allowed lower absolute voltages to be utilized as compared to the previously designed electrodes. This led to a question related to distribution of the plasmid and area being treated. Since the heating is more uniform and the electric field better distributed, it enhances delivery further by distributing the agent more uniformly. The groups tested were as follows: 45V pulses in a 4×4 manner with no heat applied and 72 pulses; 45 V in a 2×2 with heat and 36 pulses applied; 35V pulses in a 4×4 manner with heat and 72 pulses; and injection only without pulses. For each delivery condition (group), DNA was injected at 50 µl or 100 µl at a concentration of 0.5, 1.0 or 2.0 mg/ml. The best results were obtained utilizing a 100 µl injection volume at a concentration of 1.0 mg/ml. (FIG. 4)

Figure 5:
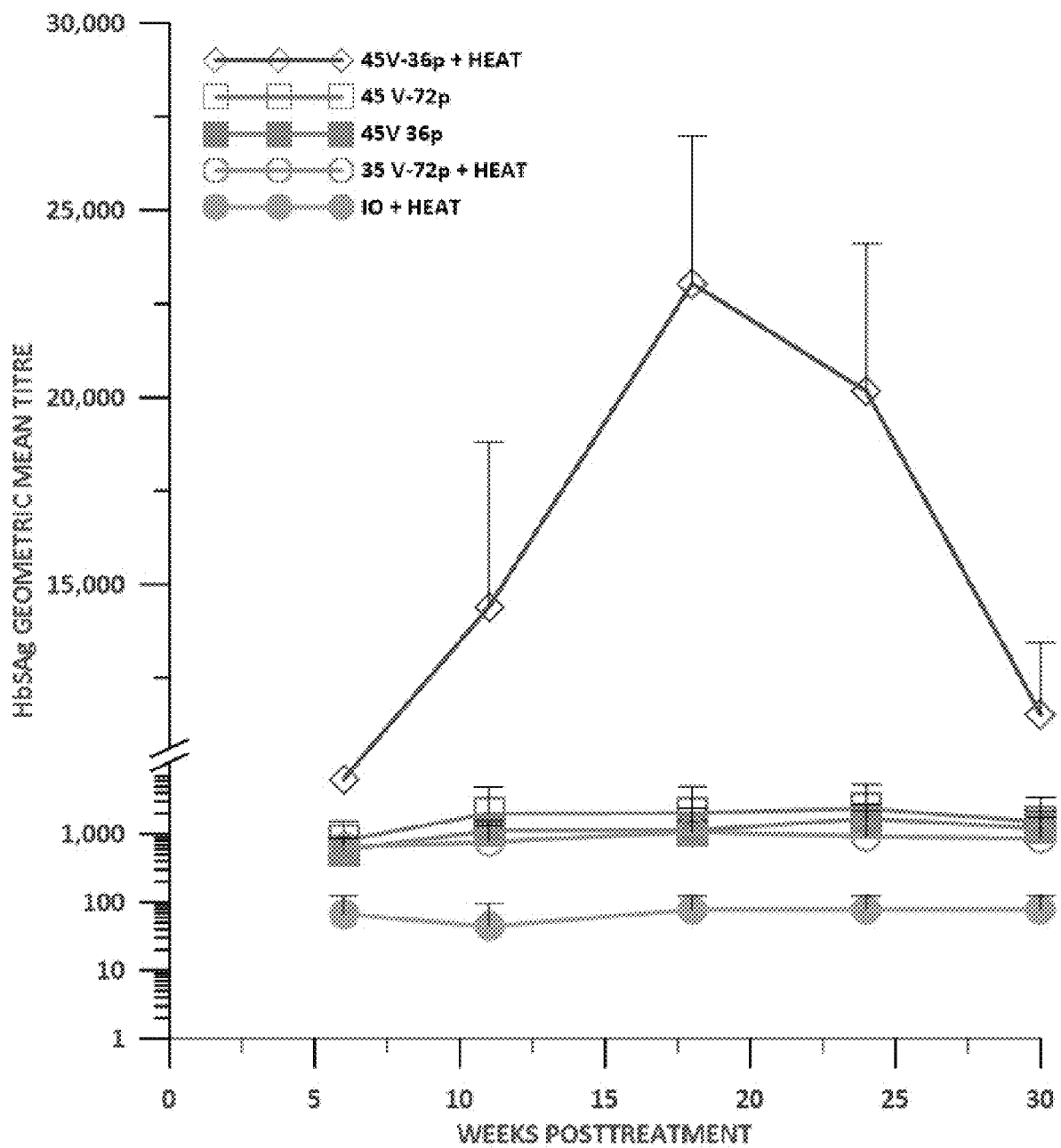
FIG. 5 is a graph depicting delivery of Hep B vaccine with combination of heat and GET. Plasmid encoding HepBSAg was delivered to the skin using GET with or without heat. GET conditions are shown in legend. N=5 for each group.

As shown in FIG. 5, plasmid encoding HepBSAg was delivered to the skin using GET with or without heat. The inventors evaluated the MEA with incorporated heating source for its potential to deliver a vaccine for Hepatitis B. We use the same plasmid for HepBSAg as described above. As shown in FIG. 5, Ab production is significantly elevated when delivery is performed with moderate heat. There was over a 10-fold increase in the level of antibodies produced. These results clearly demonstrate the utility of this approach to enhance delivery with reduced or no impact on the treated tissue.

Figure 6:
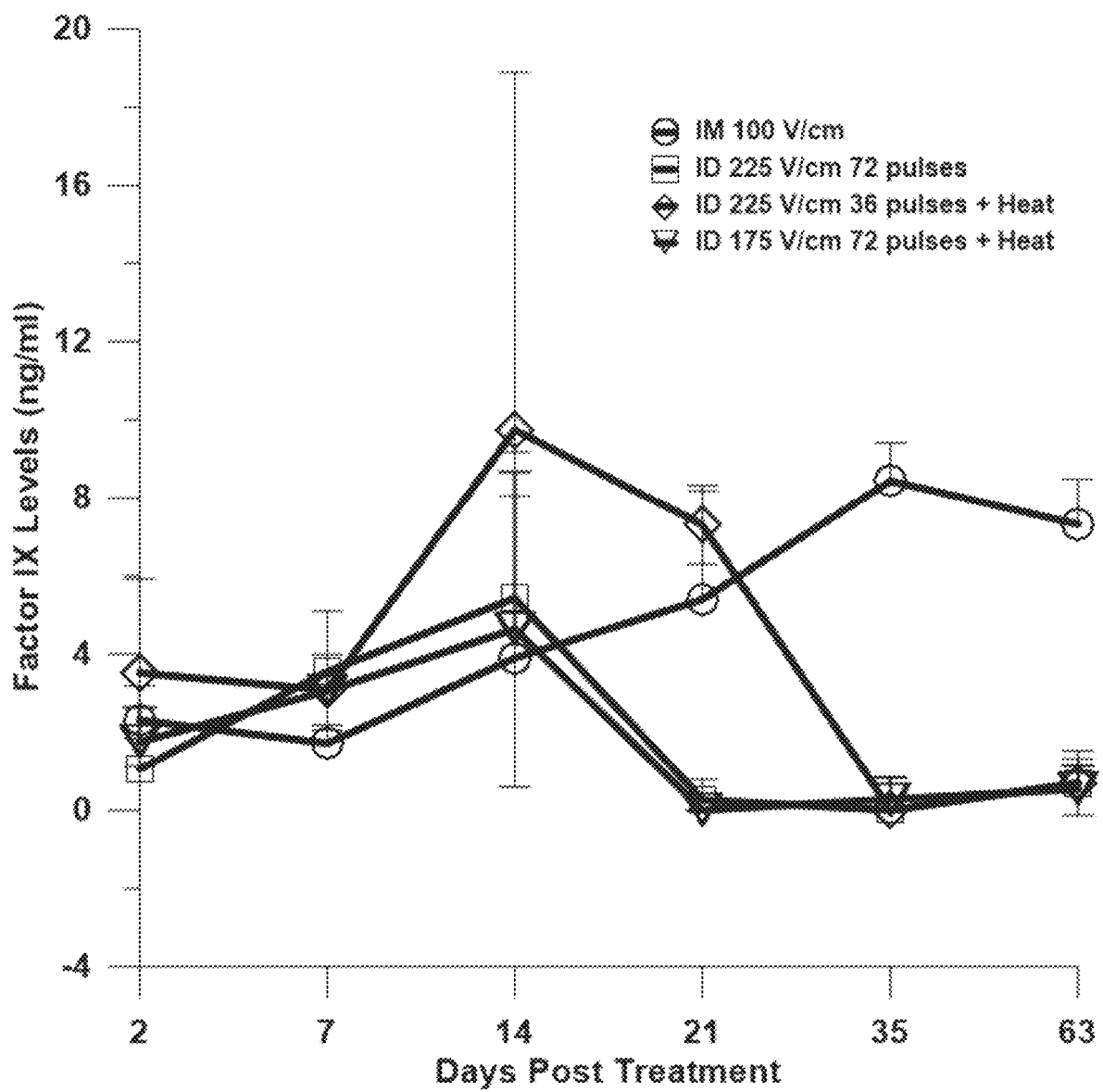
FIG. 6 is a graph depicting phFIX Delivery to skin and muscle. Human factor IX in hGP plasma. Delivery groups, IM: 50 µL DNA at a concentration of 1 µl/µl, 12 pulses at 20 ms and 100 V/cm using a 4 needle electrode array and no heat; ID 225 V/cm 72 pulses: 100 µL DNA at a concentration of 1 µl/µl+GET with 150 ms pulses as described and no heat; ID 225 V/cm 36 pulses: 100 µL DNA at a concentration of 1 µl/µl+GET with 150 ms pulses as described+heat; ID 175 V/cm 72 pulses: 100 µL DNA at a concentration of 1 µl/µl+GET with 150 ms pulses as described+heat. Bars represent mean±SD. N=4 for each group.

As shown in FIG. 6, the inventors evaluated enhancement of plasma levels of hFIX utilizing the heat+GET delivery approach. An intradermal injection of 100 µl of phFIX at a concentration of 1 µg/µl was administered followed by application of GET (single application) at various conditions. GET plus heat was accomplished utilizing the MEA-9 fiber device (FIG. 2). Comparison was made between injection only, GET without heat, GET delivery to muscle and GET with heat at two conditions. GET with heat delivered to the skin with a reduced number of pulses resulted in the highest plasma levels of FIX. Levels reached a peak of 9.74 ng/ml with these delivery conditions (FIG. 6). It also lasted a full week longer than GET without heat. The longest expression was achieved with delivery to the muscle, although the levels were not higher than with skin delivery with a peak level of 8.43 ng/ml.

While manipulating temperature has led to improvements, preheating still employs a fixed set of pulses and thus cannot compensate for differences in tissue treatment site between individuals, differences in the amount of electrical energy delivered caused by errors by the person applying the electrodes to the tissue; or differences within each segment of tissue covered by the electrodes. Compensating for these differences requires a customized method of applying pulses that can be changed for each individual treatment site or sector in the MEA.

Example 2—Impedance Feedback Pulsing Increases Expression

Data showing the use of impedance as a feedback control mechanism for applying pulses in vivo for electroporation mediated delivery has not previously been published. There are some relevant studies that used impedance spectroscopy as a means to characterize the electro-physiological condition of tissue after pulsation, but these studies did not suggest using the information to modify or control the electrical treatment. Impedance measurements can be performed using the same electrodes that are used to apply electroporative pulses without negatively impacting tissue characteristics [Connolly, R, et al, IEEE Transactions on Dielectrics and Electrical Insulation, 2009, Ivorra, A, et al, Bioelectrochemistry, 2007]. Impedance measurements require very low power compared to higher power pulses for EP. Dual use of the electrodes is ideal as it reduces the number of required electrodes and measures tissue responses directly at the electrodes used to apply EP pulses.

Impedance spectroscopy was first used to monitor irreversible electroporation in rat liver [Ivorra, A, et al, Bioelectrochemistry, 2007, Granot, Y, et al, Phys Med Biol, 2009]. The technique showed that it was possible to distinguish between reversible and irreversible electroporation in murine fibrosarcomas in vivo [Ivorra A, Phys Med Biol, 2009] Studies performed ex vivo on rat lungs and cadaver skin [Pliquett, U and Prausnitz, M, Methods Mol Med, 2003] showed that impedance changes are measurable following EP, indicating that these electrical changes could be used as an indicator of successful electroporation [Dean, D A, J Electrostat, 2008, Mossop, B J, Ann Biomed Eng, 2006]. Impedance changes in tissues have been related to the delivery of macromolecules. Persson et al. showed changes in impedance could be correlated to delivery of diethylene triamine pentetic acid (DTPA). In this study, technetium labeled DTPA was delivered to rat muscle, while impedance was measured over the frequency range of 1 kHz-10 kHz [Grafstrom, G, et al, Cancer Biother Radiopharm, 2006]. In another study pDNA was delivered to mouse muscle with multiple EP pulses. Impedance changes were observed following each pulse. However, these investigations did not relate impedance change to expression of delivered pDNA [Zampaglione, I, et al, J Gene Med, 2005]. Impedance changes have the potential to be implemented as a means of assessing EP and controlling the pulse application process in real-time. However, to date a system using a closed-loop feedback control system for EP has not been demonstrated in the scientific literature.

System for Impedance Measurement and Pulse Generation

The inventors developed a custom electroporation pulse generator and impedance spectrometer, both of which were integrated into a computer control system. A version of the 16 MEA that did not apply heat was used as the electroporation device to deliver pDNA to the tissue. The integrated device comprises both a system for applying the electrical pulses necessary to achieve electroporation within the cells/tissue and a system for measuring impedance of the cells/tissue. The measured impedance was used as a feedback control for the electroporation protocol that can be implemented during and/or after the application of each electrical pulse to customize the electrical treatment for a particular cells/tissue. The system to measure the impedance of the tissue utilizes many of the same components of the system required for performing electroporation, thereby allowing for the design of an integrated device effective for performing both impedance measurement and electroporation delivery. The electric field generation and impedance measurement instrumentation are combined into a single composite instrument that permits impedance spectra to be obtained before and/or after electric field pulses have been applied, using the same electrode array. This arrangement assures that the electric field and the impedance measurement occur in the same tissue region. The high voltage pulse delivery system and the low voltage impedance measurement system of the hardware are coupled to a computer processing system running associated software for controlling the instrument and for processing the measured impedance data. The software can control the creation of, and distribution of, electroporation pulses through the electrode array. The software can also control the measurement of the impedance of the tissue, both before and after the electroporation pulses have been applied. Comparison of impedance values after each successive electroporation pulse was used as criteria for either continuing the electroporation pulsing or discontinuing the pulsing, depending upon how much the impedance had dropped. All work was done at ambient temperature.

Delivery of pDNA to Skin of BALB/c Mice Using a 4×4 Pulsing Process

The first experiment conducted after constructing the instrumentation and calibrating/validating was to deliver pDNA encoding luciferase (gWiz-Luc, Aldevron, Fargo, N. Dak.) to the skin of BALB/c mice. The experimental scheme consisted of eight experimental groups (n=12). Six of these were injected with pDNA (100 µg in 50 µl saline, intradermally) followed by either 100, 150, 200, and 250 V/cm pulses that had a duration of 150 ms per pulse. Pulses were applied with the 16 MEA, and successive pulses were applied with 500 ms between them. Impedance data ranging from 10 Hz to 100 kHz were taken after injection and before any pulses were delivered from each sector. Post-pulse impedance spectra were taken immediately after 4×4 pulsing of each sector. The remaining two groups received either no treatment or pDNA injections only. The resulting luciferase expression was quantitated using standard Xenogen analysis on days 2, 4, 7, 10 and 14 post treatment. Mean expression was the highest for animals that received 200 V/cm pulses for 4 of the 5 timepoints. This field strength was deemed optimal for this experiment. 250 V/cm pulses resulted in significant necrosis therefore, this field was eliminated from future use.

Figure 7:
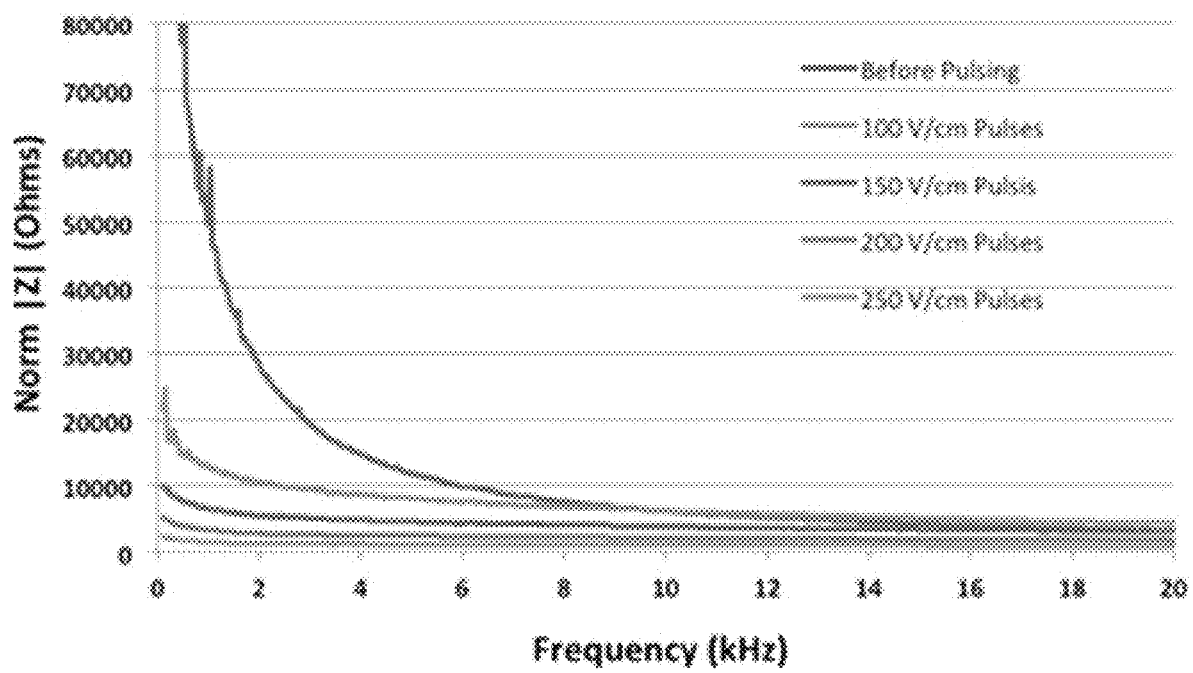
FIG. 7 is a graph depicting impedance before and after EP at 100, 150, 200, or 250 V/cm with a non-penetrating multiple-electrode array on murine skin. This plot demonstrates the effects of increasing electric field strength on impedance measurements.

The inventors found that the biggest changes in impedance due to electroporation were in the low frequency range. Post-pulse spectra showed very large decreases in the 10 Hz to 4 kHz range as compared to injected but unpulsed skin. (FIG. 7) These decreases made this range a suitable candidate to use for feedback control. Examination of many spectra revealed that there tended to be noise and/or variations in the data at frequencies below 1 kHz. Similarly, impedance reductions appeared to be less above about 4 kHz. The range of interest was further refined to be from 1 kHz to 3 kHz. The mean reduction in resistance over this range was subsequently used as a feedback control parameter to adjust pulsation and expressed as a percentage reduction of the pre-pulse impedance value over this same frequency range.

The inventors also found that animals with the highest biological responses (highest luciferase levels) had the highest percentage reduction in mean impedances in the 1 kHz-3 kHz range relative to their corresponding pre-pulse impedance values. High responders, regardless of the electric field strength used for electroporative delivery, had final mean impedance values that were reduced by 80% or more relative to pre-pulsed values. The identified 1 kHz to 3 kHz range and 80% or more mean reduction in this range were used as a feedback parameter and to establish minimum impedance reduction for use in the next set of experiments.

Delivery of Luciferase Encoding DNA to Tissue Using a Variable Pulsing Process

The potential benefits of feedback control were investigated by delivering luciferase encoding DNA using the 16 MEA and applying pulses sequentially in sectors 1 through 9 just as in the previous experiment. However, pulsation was not fixed to a 4×4 process. Instead, one pulse was applied to each sector followed by another pulse normal to the first pulse. Impedance was then measured and compared to the pre-pulse impedance of that sector. If the impedance (mean of 1 kHz-3 kHz range) was reduced by a prescribed percentage, then the pulse generator was programmed to move on and begin pulsing the next sector. If the impedance was not reduced by the prescribed percentage, then another series of two pulses were applied to the sector and impedance was measured again to determine if the mean 1 kHz-3 kHz impedance was reduced to the prescribed level. Pulsing, measuring, and comparing impedance was continued until mean impedance was reduced to the prescribed level or until a maximum of 20 sets of two pulses were applied to a sector. The minimum number of pulses that a sector could receive was 1 set of two pulses. Delivery was performed using 150, 200, and 250 V/cm pulses that were 150 ms in duration (500 ms apart). For each of these fields, delivery was performed in three different groups. For the first group, pulsing was continued until impedance dropped to 80% of the pre-pulse value in each sector. The second group has each sector pulsed until an impedance reduction of 95% was achieved. The third group received standard 4×4 pulsing for comparison. The 80% impedance reduction value was selected as it was the minimum mean reduction that resulted in high expression regardless of field strength. The 95% impedance reduction value was selected because it was close to a complete reduction of impedance. It was established that the low 1V signal used to measure impedance did not affect delivery.

Results are shown in FIG. 8 with 8A through 8C showing plots of mean radiance of animals (n=12, proportional to luciferase levels) versus time for each individual field strength. Plot D shows all data together for perspective. In view of the data, the inventors found that feedback based pulsing to 80% and 95% reductions in impedance produced higher peak and total expression than standard pulsing for all electric fields (FIG. 8A-8C). The 100 V/cm and 150 V/cm feedback control groups had data that were statistically different ($\alpha=0.05$) when compared to respective 4×4 pulsed groups at about half of the time points. Both the 80% and 95% feedback data were statistically different than the 4×4 pulsed group at 200 V/cm for days 7, 10 and 14. The data also showed that every feedback condition resulted in higher expression than 100, 150, 200 V/cm standard pulses. Thus, feedback resulted in an improvement every time at every field strength. (FIG. 8D).

The inventors also found that peak expression from feedback pulsing scenarios were 6-15 fold higher than their respective standard pulsing. The data showed that feedback pulsing with 100 V/cm suboptimal pulses (based on traditional optimization) resulted in higher peak and total expression that traditionally optimized pulsing at 200 V/cm. The number of pulses applied varied even within like-treated feedback animals which indicates that the device and algorithm was working and could compensate for differences in individual treatment sites. These data support that a feedback strategy based upon achieving a prescribed decrease in pre-pulse impedance in the 1 kHz to 3 kHz range was successful. This type of control strategy can drive the system to higher delivery/expression regardless of the starting point (i.e. suboptimal field).

Given the success of the feedback method, impedance data and electrical current data from many animals were examined to look for other characteristics that could indicate successful delivery. The inventors found differences between those with high biological responses and those with low responses. When impedance data was examined as its real part vs. reactance part as Nyquist plots, it became clear that high responders had distinguishable reactance changes. (data not shown) These changes could be attributed to capacitive changes, likely due to cell membrane breakdown, after fitting to a standard mathematical circuit model. In addition, the quantity of electric current flow was measured during every pulse. These data showed that generally higher current yielded higher expression levels. The changes in reactance and strength of electric current can be used as additional impedance feedback parameters. These two differences both relate to property changes of the tissue due to the electroporation pulses.

Example 3—System for Monitoring Both Impedance and Temperature

Gene therapy is a maturing field with increasing successes in clinical applications. Even with these successes there is still a major distinction between a gene based therapy and a protein based therapy with the distinction being control of the therapeutic dose. Protein based drugs allow for defined dose based on pharmacodynamics, pharmacokinetics and defined levels needed to obtain a therapeutic dose. With a gene based approach the delivered molecule is the transgene, in a carrier, and not the actual therapeutic protein. One must rely on reproducible expression with respect to levels and kinetics to achieve the appropriate dose. Being able to come closer to controlling those aspects with a delivered gene would move gene based therapy closer to protein based therapy and potentially improved therapeutic outcomes and reduced adverse effects.

It is evident from previous work that significantly higher levels of plasmid expression can be obtained by injecting plasmid DNA followed by electric pulses than by plasmid injection alone. It is also clear that by understanding the electrical properties of the delivery site before, during, and after electric pulses are administered could allow for a high level of control and reproducibility achieved by monitoring impedance changes at the delivery site. Temperature modulation can also be used to better control and direct delivery. Thus, control and enhanced reproducibility are the major achievements of this system.

The exemplary system is comprised of an electroporation device capable of heating the skin and monitoring temperature coupled to a computer controlled impedance analyzer/pulse generator capable of integrating feedback control for pulsing based upon impedance data and controlling temperature based upon temperature measurement.

Prophetic Electroporation Device

In an exemplary embodiment, a 16 MEA is manufactured in order to incorporate both heating and temperature measurement components along with the application of electric fields to induce electroporation and gene electrotransfer. Sixteen electrodes 105 are arranged in a 4×4 array on removable circuit board 110. The exemplary 4×4 array is comprised of sixteen electrodes 105 configured into 9 sections with each section comprising four electrodes, similar to the array shown in FIG. 2. The optic fibers (solid dots) shown in FIG. 2 may be replaced with at least one alternative heating element in some embodiments. In such embodiments, instead of optic fibers positioned in the center of each sector of electrodes, a plurality of light emitting diodes (LEDs) may be disposed within handle 130 of device 100 proximal to electrodes 105. While a 16 MEA is described, any configuration of at least two electrodes may be used.

Electrodes 105 may be gold plated 0.5 mm diameter rods that are affixed to through apertures by solder. Each electrode in the application may be spring loaded, which allows the tips to conform to differences in animal skin topology, ensuring that the electrodes maintain good contact with the tissue of interest. Electrodes 105 may be flat bottom, non-penetrating electrodes that are spaced between 2.0 to 2.5 mm apart, center to center, thus creating a square geometry. The array created nine 2.0 mm by 2.0 mm or 2.5 mm by 2.5 mm square spaces between electrodes, with each spacing referred to as a sector of treated tissue.

Figure 9:
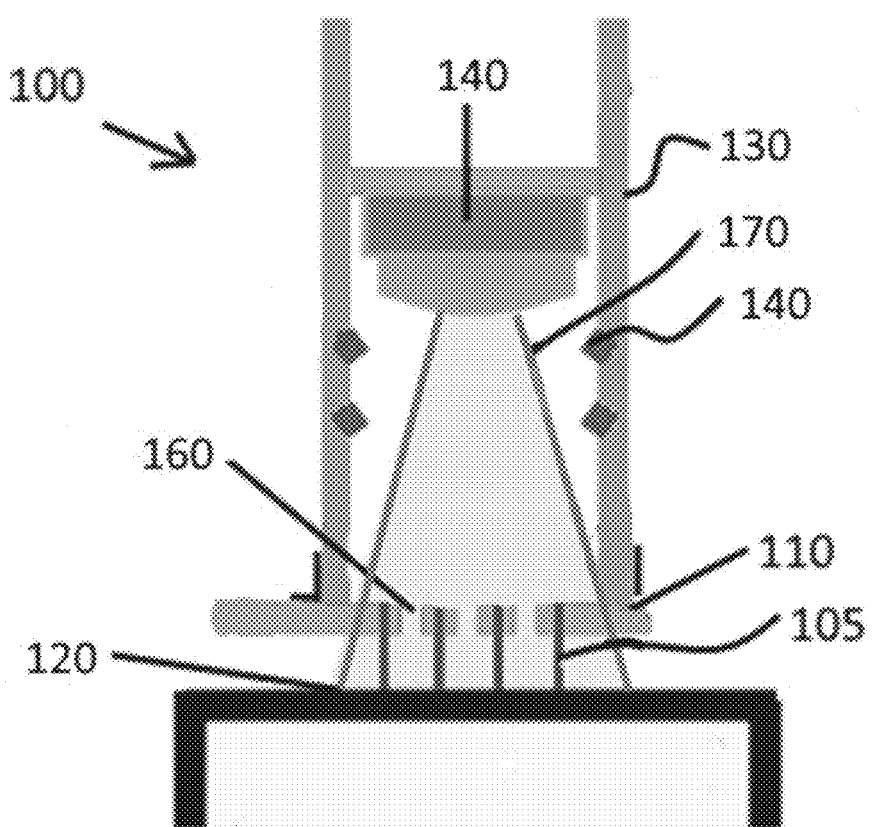
FIG. 9 is a cross-sectional image of a 16 MEA electroporation device that includes infrared (IR) LED heating elements and thermal imaging.

As shown in the embodiment of FIG. 9, electrodes 105 extend from first side of circuit board 110 by about 5 mm to contact tissue 120. Electrodes 105 are flush with second side of circuit board 110 which faces interior of handle 130. Through apertures are connected to edge connector via metal traces in circuit board 110 to provide independent electrical connection for each electrode 105. Circuit board 110 is connected to machined handle 130 which can be tubular in shape comprising an interior and an exterior. Interior of handle 130 contains heating elements 140 as well as a temperature measurement system 150 such as a small IR sensing camera. In some embodiments, circuit board 110 may be made of glass or a polymer that is transmissive of IR.

Heating elements (heat generation device) 140 can be any device capable of producing heat by any means known in the art. Heating elements 140 are preferably capable of being contained within interior of handle 130. In some embodiments, an array of far infrared light emitting diodes (LEDs, such as LED36-SMD5R, Roithner LaserTechnik) are used as heating elements 140. Far infrared (wavelengths of 3 μm to 1 mm) is preferably used for heating in an embodiment because far infrared transmits deeper into the tissue. There is evidence that far infrared is absorbed better by water which comprises the bulk of living tissues. [Soyun Cho, Mi Hee Shin, Yeon Kyung Kim, Jo-Eun Seo, Young Mee Lee, Chi-Hyun Park and Jin Ho Chung, Effects of Infrared Radiation and Heat on Human Skin Aging in vivo, Journal of Investigative Dermatology Symposium Proceedings (2009) 14, 15-19]. Device 100 can contain multiple arrangements of LEDs as long as they are capable of efficiently heating tissue 120 surface to a preset temperature in about a minute or less. The arrangement and direction of emission can vary according to the distribution of temperature. In some embodiments, the capacity to turn heating elements 140 on individually or in clusters can be implemented to allow better control of heating. For example, "cooler" sectors or larger areas can be exposed a little longer or possibly with more LED's directly emitting toward them.

Temperature of tissue 120 is determined by a temperature measurement system 150 such as thermal images from a small IR sensing camera that can be located on small circuit boards capable of fitting into hollow handle 130. An example of such a camera is a forward looking infrared radiometer (FLIR), however any small IR sensing camera may be used. In this embodiment, camera is positioned a few cm above the proximal end of electrodes 105 which are flush with circuit board 110. Tissue 120 surface is the focal plane of camera. Heating elements 140 are arranged to emit heat toward tissue 120 surface. Orifices 160 are positioned in circuit board 110 at the center of each sector, which is located between each set of 4 electrodes 105. Orifices 160 allow for free passage of the IR even though it may pass through circuit board 110, with some attenuation, if there were no orifices 160.

Method of Use

Device 100 is used to uniformly increase skin surface temperature to a maximum of 50° C. in about 60 seconds. The number and arrangement of the LED's is empirically determined by heating guinea pig skin and monitoring the process with the FUR camera. Three animals are utilized for this testing. Temperature measurements are made with the LEDs off momentarily to determine this time using a computer control system. Images of the skin surface appearing through orifices 160 in circuit board 110 (i.e. of the skin between each set of 4 electrodes/sector) are used. Thermal image 170 is processed to isolate the temperature of the skin surface in each sector with the aid of a superimposed white light image. "Subtracting" these two images yields the temperature of the skin surface in each sector. The control system algorithm allows the user to input a set temperature, allow the skin to increase to that temperature, turn the LED's off, and then periodically check the temperature to provide a brief period of heating to maintain the temperature when necessary.

Alternative Electroporation Device (Non-Prophetic)

Figure 10:
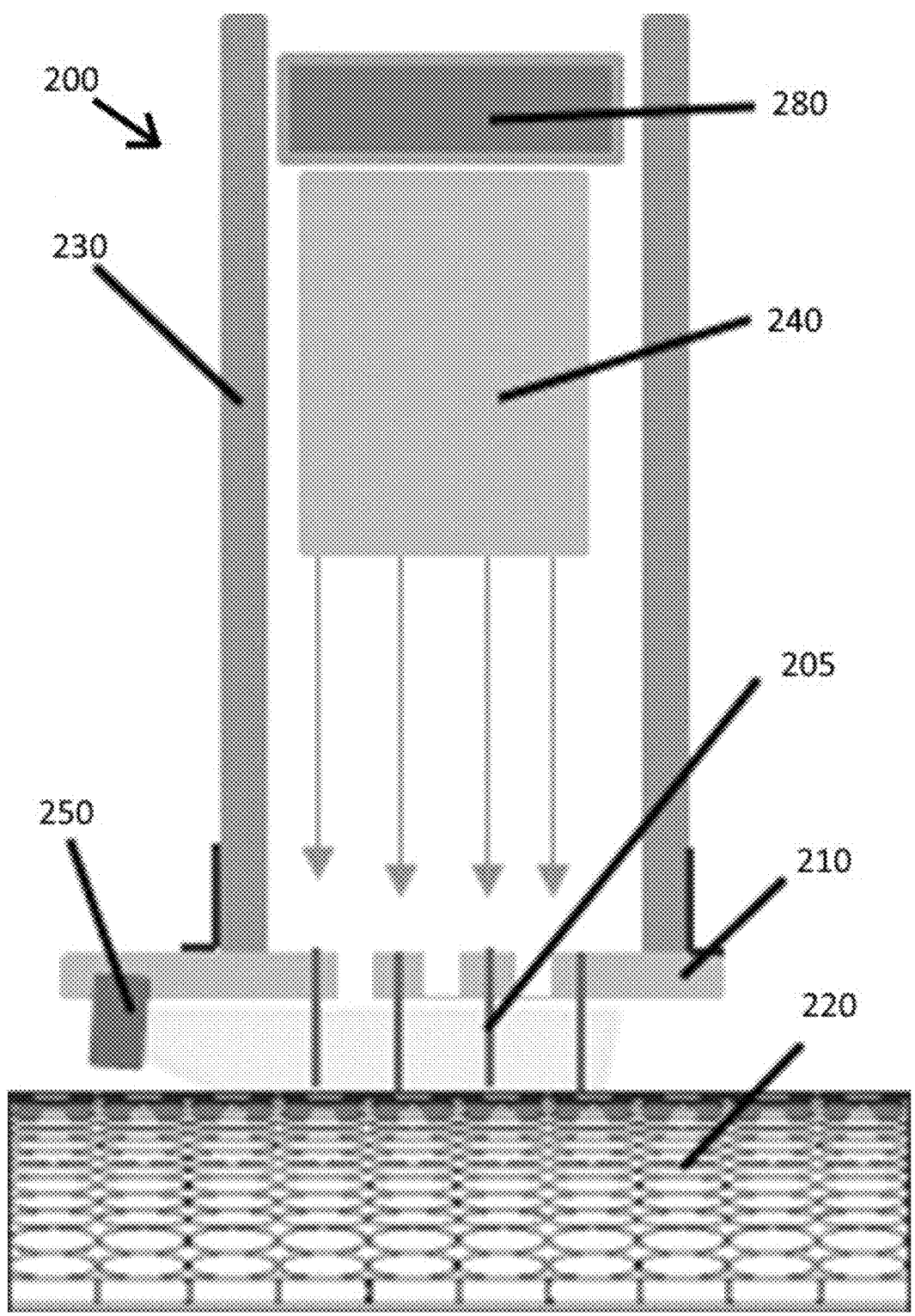
FIG. 10 is a cross-sectional image of a 16 MEA electroporation device that includes a fan positioned above a heating element to blow warm air over the surface of the target tissue to heat the target area. The arrows represent the warm air being directed at the target tissue. In this embodiment, the temperature measurement device is positioned on the exterior of the handle as opposed to being within the handle.

In an alternative embodiment, device 200 shown in FIG. 10, heating element 240 was positioned distal to fan 280, both of which were contained within handle 230. Temperature measurement system 250 was positioned outside of handle 230 to measure temperature of tissue 220. The arrows in the figure represent warm air (heat) generating from heating element 240 and being blown toward tissue 220 by fan 280 to heat tissue 220.

The method of use of this embodiment of the electroporation device is similar to that discussed above in which electrodes 205, which are attached to circuit board 210, are in contact with tissue 220 to deliver electrical pulse(s) to tissue 220. Fan 280 is used to direct warm air from heating element 240 towards tissue 220 surface to heat tissue 220 surface. Minor differences as to measuring temperature are made to account for the placement of temperature measurement system 250 outside of handle 230 however, generally the thermal image is processed to isolate the temperature of the skin surface in each sector with the aid of a superimposed white light image. "Subtracting" these two images yields the temperature of the skin surface in each sector. The control system algorithm allows the user to input a set temperature, allow the skin to increase to that temperature, turn the heating element off, and then periodically check the temperature to provide a brief period of heating to maintain the temperature when necessary.

Alternative Electroporation Device (Non-Prophetic)

Figure 11:
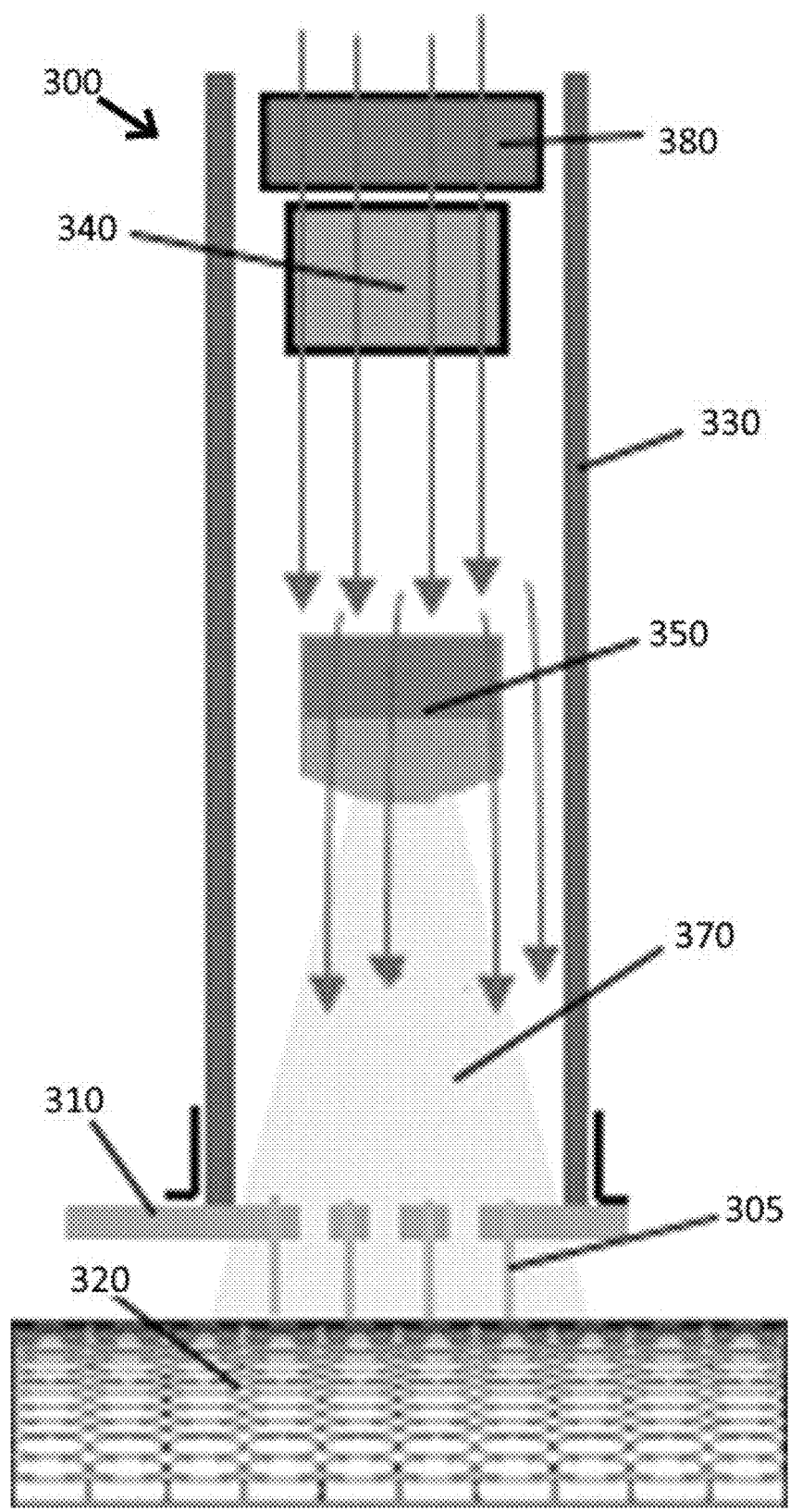
FIG. 11 is a cross-sectional image of a 16 MEA electroporation device that includes the fan and heating element of FIG. 10 but positions the temperature measurement device within the handle as in FIG. 9.

In a further embodiment, device 300 shown in FIG. 11, both heating element 340 and temperature measurement system 350 were contained within handle 330. Heating element 340 was positioned distal to fan 380 (similar to FIG. 10) to allow warm air to be directed towards tissue 320. Temperature measurement system 350 was positioned within handle 330 between heating element 340 and tissue 320 so that thermal image 370 is capable of being processed by temperature measurement system 350.

The method of use of this embodiment of the electroporation device is similar to that discussed above with respect to FIG. 9. Fan 380 is used to direct warm air from heating element 340 towards tissue 320 surface to heat tissue 320 surface. Electrodes 305, attached to circuit board 310, are in contact with tissue 320 to allow for delivery of the electrical pulse(s). Thermal image 370 is processed to isolate the temperature of the skin surface in each sector with the aid of a superimposed white light image. "Subtracting" these two images yields the temperature of the skin surface in each sector. The control system algorithm allows the user to input a set temperature, allow the skin to increase to that temperature, turn the heating element off, and then periodically check the temperature to provide a brief period of heating to maintain the temperature when necessary.

Impedance Spectrometer/Pulse Generator System

The impedance spectrometer/pulse generator is comprised of a custom relay board, computer used as a controller, software, and impedance spectrometer. Relays, or similar switching devices, are used to direct electric pulses to the individually addressable electrodes 105, 205 and 305. In some embodiments, in which there are sixteen electrodes in the MEA, there are thirty-two isolated solid state relays that are controlled by a data acquisition and control module. In this embodiment, sixteen of the relay are connected to a positive terminal while the remaining sixteen relays are connected to a ground terminal of a high voltage power supply. An impedance spectroscope and an electric field generator are coupled to the solid state relays. The impedance spectroscope may include an I/O card for generating a multi-frequency sine analog voltage reference signal buffered by a unity gain high-bandwidth amplifier rated to drive capacitive loads. A pair of instrumentation amplifiers may be coupled to the I/O card of the impedance spectroscope to measure a differential voltage across, and current flowing through, a tissue sample and to buffer the measured results. In some embodiments, the impedance spectroscope operates at a low frequency. In a particular embodiment, the sampling rate for both the reference signal generation and the voltage/current measurements may be about 1 MHz. The electric field generation and impedance measurement instrumentation are combined into a single composite instrument that permits impedance spectra to be obtained before and/or after electric field pulses have been applied, using the same electrode array. This arrangement assures that the electric field and the impedance measurement occur in the same tissue region. In this embodiment, the solid state relays are used to rapidly connect and disconnect the high voltage pulse delivery instrument and the low voltage impedance measurement portion of the instrument. The solid state relays, the high voltage pulse delivery system and the low voltage impedance measurement system of the hardware are coupled to a computer processing system running associated software for controlling the instrument and for processing the measured impedance data. The software may control the creation of, and distribution of, electroporation pulses through the electrode array. The software may also control the measurement of the impedance of the tissue, both before and after the electroporation pulses have been applied. The software may also control the use of the heat generating device, such as IR LEDs, and temperature measurement device, such as an FUR camera, with temperature control and image processing software being integrated into the main software for pulsing and impedance. Comparison of impedance values after each successive electroporation pulse may be used as criteria for either continuing the electroporation pulsing or discontinuing the pulsing, depending upon how much the impedance had dropped.

Following assembly of the system, it is bench-top tested to ensure functionality and accuracy with the system being tested to ensure that the temperature maintenance routine is comparable to results obtained with other temperature measuring devices. To determine accuracy of the impedance portion of the system, a potentiostat meeting NIST calibration standards (Gamry, Warminster, Pa.) is used along with other precision electronic components to create circuits with known impedance characteristics. For the pulse creation circuitry, high voltage pulses are captured with an oscilloscope to ensure the system is outputting the proper pulse width and voltage, and can sustain the power required to produce square wave pulses in tissues. The very low voltage output of the impedance circuitry is captured with an oscilloscope to verify the excitation signal voltage and duration. Oscilloscope measurements are used to ensure the system switches properly between pulsing and impedance measurement mode. The capacity to use impedance measurements to alter pulsation is built into the software.

The present invention may be embodied on various computing platforms that perform actions responsive to software-based instructions. Instructions stored on a computer readable medium may be utilized to enable the invention. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object oriented programming language such as Java, C#, C++ or the like and conventional procedural programming languages, such as the "C" programming language or similar programming languages.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Example 4—Delivery of DNA while Monitoring Temperature and Impedance (Prophetic)

The inventors use the system described in Example 4 to determine if the combined use of elevated temperature and customized pulsing can improve the control and reliability of the electrotransfer process. Based on preliminary data it is clear that skin impedance changes result from electropulsation at ambient temperature (~35° C.). Impedance changes likely occur at elevated treatment temperatures however, it is unknown if these changes are the same at ambient temperatures. Impedance-feedback based pulsing relies on identifying and quantitating these changes during pulsation, thus these changes must be identified at elevated temperatures. After identification, system programming is modified to use these changes as a parameter for feedback control. Feedback control is then used to deliver reporter plasmids to determine if controlling delivery can result in higher/longer expression, require fewer pulses, and/or be achieved using lower voltages as compared to existing optimized delivery parameters at ambient temperature. It is thought that this approach results in reproducible delivery between animals.

Prophetic Example to Deliver Plasmid DNA to a Tissue

The flank skin of mixed sex Hartley Guinea pigs and luciferase encoding plasmid DNA (gWizluc, Aldevron, Fargo, N. Dak.) are used for the experiments. Each animal has 4 treatment sites, two on each flank, treated. Post-treatment impedance spectra from animals treated at 4 temperatures using 4 different electric fields (pulse voltage/distance between electrodes) is collected. Analysis of the spectra from animals with high luciferase levels enables identification of impedance and other changes that correlate with higher expression/delivery. In particular, spectra are examined to determine what changes in low frequency, capacitive, and current changes (electrical flow) are used as parameters for feedback control. Software is modified to employ feedback control based on the three identified parameters with each parameter used to deliver plasmid DNA. Any histologic effects and the location of the expressed DNA using delivery conditions that resulted in the highest expression is examined.

Impedance changes due to temperature and pulsation are determined by delivering gWizLuc to the flank skin of bilaterally shaved guinea pigs. DNA is introduced into the skin of each treatment site by intradermal injection of 50 µl saline containing 100 µg DNA. A set of 6 treatment groups have DNA delivered at 4 different temperatures. The treatment groups include no treatment (no DNA or pulses), DNA injection only (no pulses), and DNA delivered with 45V, 35V, 25V, or 15V in a 4×4 manner. These voltages correspond to 225 V/cm, 175 V/cm, 125 V/cm, and 75 V/cm (voltage divided by 0.2 cm distance between electrodes=V/cm). This set of six treatment groups is treated at ambient skin temperature (measured) and also at 40° C., 43° C., and 46° C. Each of these conditions is used to treat 8 sites per group. [Heller R, Cruz Y, Heller L C, Gilbert R A, Jaroszeski M J. Electrically mediated delivery of plasmid DNA to the skin, using a multielectrode array. Hum Gene Ther. 2010; 21(3):357-62; Ferraro B., Heller L. C., Cruz Y. L., Guo S., Donate A., Heller R., Evaluation of delivery conditions for cutaneous plasmid electrotransfer using a multielectrode array. Gene Ther. 2011 May; 18(5): 496-500; Guo S., Donate A., Basu G., Lundbert C., Heller L., Heller R., Electro-gene transfer to skin using a noninvasive multielectrode array. J Control Release. 2011, May 10: 151(3): 256-262; Guo S, Israel A L, Basu G, Donate A, Heller R Topical Gene Electrotransfer to the Epidermis of Hairless Guinea Pig by Non-Invasive Multielectrode Array. PLoS ONE 2013, 8(8): e73423]. All pulses are 150 ms in duration with 150 ms between successive pulses. Impedance spectra is taken from each animal before treatment, after injection, and again after 4×4 electroporation pulses. Each spectra is taken from 10 Hz to 100 kHz. Electrical current data during EP pulsation is recorded. Luciferase expression levels are evaluated on 2, 4, 7, 10, 14, 21, and 28 days post-treatment. Based upon experience and the literature, this schedule will capture peak expression and by day 21 expression is close to animals that only received DNA injection. Peak and total expression (for 28 days) is considered when analyzing the data with respect to impedance changes. In general, mean luciferase levels are analyzed to look for trends with respect to temperature and applied field.

Post-EP impedance spectra are examined from the highest responders regardless of field strength used for treatment or temperature. The spectra are analyzed for characteristics that correlate to high luciferase levels as measured using a Xenogen instrument. From the preliminary data it is likely that a reduction in impedance data (|Z|) under 40 kHz is a strong correlate to luciferase levels. Data is examined to determine if spectra from high expressers can be correlated with some feature or change in capacitance (using Nyquist plots) and if a relationship between current change and high expression is identified. Current generally increases with each successive pulse, thus a current threshold for high responses may be identified. These changes/features are each used as feedback parameters. The three parameters are an impedance drop of X relative to pre-pulse impedance in a small range of frequencies, a capacitance change of Y (likely a decrease) relative to pre-pulse values, or a minimum threshold current of Z during electropulsation.

Luciferase encoding plasmid is delivered to skin as described above. However, a feedback style of pulsing is used to treat groups of animals (N=8 treatment sites). The impedance drop parameter (X) identified previously is used along with two of the highest performing electric fields. Fields are selected based upon highest mean and integrated luciferase levels. These are used to apply feedback pulsing using all of the temperatures. As described above, feedback pulsing involves pulsing until the predetermined impedance drop (X) has been achieved in each treatment sector while maintaining the temperature. Standard 4×4 pulsing (at both voltages) is applied for comparison along with no treatment and DNA injection only groups. The same experiment is conducted but feedback is based upon the capacitive change (Y) identified previously or the experiment uses threshold current (Z) as the feedback parameter.

Preliminary data indicated that feedback and a temperature increase from ambient to 43° C. independently increase expression. The inventors anticipate a synergistic effect because feedback optimizes/customizes pulsing in each individual sector of the 16 MEA treatment area and creates a uniform temperature distribution. The inventors expect some degree of reduced variability as was noticed in murine preliminary data which in itself is a positive as decreased variation certainly means better delivery control and thus more subjects ultimately have expression above threshold to produce a response (i.e. vaccine).

Example 5—Delivery of Plasmids Encoding Therapeutic Proteins (Prophetic)

Demonstrating the delivery system process using DNA encoding molecules that have therapeutic potential is critically important. Use of plasmid DNA for these therapeutic approaches has distinct advantages over the use of recombinant protein. The system's potential for administering two types of therapies is examined by using delivery parameters that resulted in the highest expression with negligible histologic effects. The first therapy tests the potential of a secreted protein as an example of delivering DNA that encodes a molecule that has a direct therapeutic effect. Successful delivery of a plasmid for protein replacement therapy minimizes the number of treatments. With recombinant protein, due to the half-life, patients may require frequent injections while DNA could make the interval between doses much longer. The second therapy examines delivering an encoded antigen to determine if indirect effects are possible. DNA delivery is an appealing approach to infectious disease vaccines and this has been a major area of growth for electroporation. Conventional infectious disease vaccines involve pathogen cultivation and vaccine delivery may create the potential for infection in immunosuppressed and immunocompromised individuals. DNA vaccines can be produced quickly to manage outbreaks or genetically changing organisms. These represent two commonly envisioned uses for gene therapy. Kinetics of expression is examined because long-term or short-term expression may be desirable. Long-term expression may require multiple deliveries, so the effects on the tissue integrity must be established.

Prophetic Example of Delivery of Plasmid Encoding hFIX (phFIX)

The two combinations of feedback-based parameters that lead to the highest expression levels and lowest variation above are used to deliver plasmid encoding human Factor IX (phFIX). One corresponds to the highest mean peak expression and the other corresponds to the highest mean integrated expression. Two criterion used include minimal dispersion and negligible histologic effects. If two sets of parameters have statistically indistinguishable data, the set that used the lowest voltage is chosen for use as it leads to increased patient comfort. The parameter sets include feedback parameter, voltage (field) and temperature. Optimized 4×4 pulses (45 V, 225 V/cm) at ambient temperature are used as a standard for comparison along with DNA injection at ambient temperature. Each group is comprised of 8 animals with 1 treatment site per animal. On days 0, 2, 4, 7, 10, 14, 21 and 28, blood is collected from each group. Serum is evaluated for factor IX by ELISA. Animals are followed beyond day 28 if there is still increased expression.

The experiment is repeated to determine if delivering DNA three times can maintain expression over a longer period. The repeat procedure is administered at time points coinciding with decreases in expression following a single application, likely at about 10 days. For example, treatments are performed on days 0, 10 and 20. Duration of expression is monitored, and the treated animals are observed to determine how they tolerate multiple applications. Serum is collected twice/week until levels return to background.

Prophetic Example of Delivery of Plasmid Encoding Hepatitis B Surface Antigen (pHBSAg)

Plasmid encoding Hepatitis B surface antigen (pHBSAg) is administered to guinea pigs using the same 5 treatment groups as described above. Animals are treated twice, once on day 0 and again on day 14. Blood is collected from the animals at baseline (Day 0) and then at 7, 14, 21, 28, 35 and 42 days following the first treatment. Serum is evaluated for levels of anti-HBSAg antibodies by ELISA.

Peak and integrated levels of FIX are statistically higher than with standard EP and with less variation (i.e. lower coefficients of variation and or standard deviations). The same increased efficiency and better control is shown in the anti-HBSAg antibody data. At least one condition used for feedback pulsing uses a significantly lower electric field that the standard method for pulsing at ambient temperature. If data from this lower field does result in higher FIX levels or antibody titers (peak or integrated, or both), along with lower variability, then the utility of the hardware, software, and methods are a significant advantage for delivery.

Example 6—Delivery of Vaccines and Therapeutics for Infectious Pathogens (Prophetic)

Delivery remains a key hurdle for nucleic acid-based therapeutics. Two key issues facing delivery of nucleic acid-based therapeutics: (1) the inability to immediately detect if appropriate delivery has occurred and (2) safe and efficient delivery of the therapeutic.

Non-viral gene therapies can be delivered using electroporation or electrotransfer (ET), which increases cell permeability using tightly controlled electric pulses. ET induces both humoral and cellular immunity. (Babiuk S, Baca-Estrada M E, Foldvari M, Storms M, Rabussay D, Widera G, Babiuk L A. Electroporation improves the efficacy of DNA vaccines in large animals. Vaccine. 2002; 20(27-28):3399-408). At least two (Inovio Pharmaceuticals, Karolinska Institute/Cobra Biologics) DNA vaccines using this delivery method are in clinical trials, with a third (Evvivax) in preclinical evaluation. A concern with the delivery of nucleic acid vaccines and therapeutics is achieving appropriate expression levels. A second issue with this approach is that there is not a way to know that successful delivery has been achieved.

When delivering a vaccine or therapeutic for a virulent pathogen such as SARS-CoV-2 it is critical to overcome both of these issues. ET has been demonstrated to be able to efficiently deliver nucleic acids to several critical tissue targets. Utilizing moderate heat enables the delivery to be more efficient and to be accomplished at a lower applied voltage. The vaccine(s) and therapeutic plasmids can be delivered to multiple tissue targets, specifically muscle and/or skin. Muscle would be utilized for long-term expression of the therapeutic molecule and to achieve higher systemic levels of the protein. Skin contains a higher number of antigen-presenting cells so is a better candidate for vaccine delivery. Utilizing moderate heat would enable a more controlled delivery to a specific level within the tissue and achieve a more predictable expression profile. (Donate A, Burcus N, Schoenbach K, Heller R. Application of increased temperature from an exogenous source to enhance gene electrotransfer. Bioelectrochemistry. 2015; 103:120-3; Donate A, Bulysheva A, Edelblute C, Jung D, Malik M A, Guo S, Burcus N, Schoenbach K, Heller R. Thermal Assisted In Vivo Gene Electrotransfer. Curr Gene Ther. 2016; 16(2):83-9; Edelblute C M, Hornef J, Burcus N I, Norman T, Beebe S J, Schoenbach K, Heller R, Jiang C, Guo S. Controllable Moderate Heating Enhances the Therapeutic Efficacy of Irreversible Electroporation for Pancreatic Cancer. Scientific reports. 2017; 7(1):11767; Edelblute C M, Guo S, Hornef J, Yang E, Jiang C, Schoenbach K, Heller R. Moderate Heat Application Enhances the Efficacy of Nanosecond Pulse Stimulation for the Treatment of Squamous Cell Carcinoma. Technol Cancer Res Treat. 2018; 17:1533033818802305). In addition, it enables the use of a gentler protocol that would be less painful.

To address the issue of determining if delivery has been achieved, delivery is monitored through measurement of impedance. (Connolly R J, Rey J I, Jaroszeski M J, Hoff A M, Gilbert R, Llewellyn J A. Effectiveness of Non-penetrating Electroporation Applicators to Function as Impedance Spectroscopy Electrodes. Ieee Transactions on Dielectrics and Electrical Insulation. 2009; 16(5):1348-55; Ivorra A, Rubinsky B. In vivo electrical impedance measurements during and after electroporation of rat liver. Bioelectrochemistry. 2007; 70(2):287-95; Granot Y, Ivorra A, Maor E, Rubinsky B. In vivo imaging of irreversible electroporation by means of electrical impedance tomography. PhysMedBiol. 2009; 54(16):4927-43; Ivorra A, Al Sakere B, Rubinsky B, Mir L M. In vivo electrical conductivity measurements during and after tumor electroporation: conductivity changes reflect the treatment outcome. PhysMedBiol. 2009; 54(19):5949-63; Pliquett U, Prausnitz M R. Electrical impedance spectroscopy for rapid and noninvasive analysis of skin electroporation. Methods Mol Med. 2000; 37:377-406; Dean D A, Ramanathan T, Machado D, Sundararajan R. Electrical Impedance Spectroscopy Study of Biological Tissues. JElectrostat. 2008; 66(3-4):165-77; Mossop B J, Barr R C, Henshaw J W, Zaharoff D A, Yuan F. Electric fields in tumors exposed to external voltage sources: implication for electric field-mediated drug and gene delivery. AnnBiomedEng. 2006; 34(10):1564-72; Grafstrom G, Engstrom P, Salford L G, Persson B R. 99mTc-DTPA uptake and electrical impedance measurements in verification of in vivo electropermeabilization efficiency in rat muscle. Cancer BiotherRadiopharm. 2006; 21(6):623-35; Zampaglione I, Arcuri M, Cappelletti M, Ciliberto G, Perretta G, Nicosia A, La Monica N, Fattori E. In vivo DNA gene electro-transfer: a systematic analysis of different electrical parameters. JGene Med. 2005; 7(11):1475-81; Atkins R M, Fawcett T J, Gilbert R, Hoff A M, Connolly R, Brown D W, Llewellyn A J, Jaroszeski M J. Impedance spectroscopy as an indicator for successful in vivo electric field mediated gene delivery in a murine model. Bioelectrochemistry. 2017; 115:33-40).

When using nucleic acid-based therapeutics, typically one would have to wait to see a measurable effect. This would either be measuring the expression of the transgene or observing the desired prophylactic or therapeutic effect. There can be a considerable delay in obtaining this answer, which if negative can result in loss of valuable time when dealing with a therapeutic for a deadly disease. In the case of vaccinating a large number of individuals, it will be critical to be assured that the vaccine was properly delivered prior to move to the next individual. Delivering with ET enables the use of impedance monitoring to determine if proper delivery has occurred at the time of administering the vaccine or therapeutic. This will increase the reproducibility of the nucleic acid-based medicine.

Example 7—SARS-CoV-2 Vaccine Administration (Prophetic)

Severe Acute Respiratory Syndrome Coronavirus 2 (SARS-CoV-2), the virus that causes COVID-19, has caused a global pandemic that has killed over 1 million people worldwide. The respiratory virus is spread from person to person mainly through airborne transmission from respiratory droplets or small aerosolized particles that are produced when an infected person coughs, sneezes, sings, talks or breathes. The virus can also spread when an infected person coughs on, sneezes on or touches a surface such as tables, doorknobs, handrails, etc. as the virus has been shown to live on various surfaces ranging from hours to days. There are currently no approved vaccines for the virus and only one approved therapeutic, an antiviral medication named Remdesivir.

Traditional vaccines can contain inactivated or live-attenuated whole pathogens. The pathogen culture and processing required for production of these vaccines can put the manufacturer at risk of infection. Rarely, attenuated vaccines can revert and cause infection in the recipient. The antigens for subunit vaccines can be derived directly from the pathogen or made more safely using recombinant technology in eukaryotic or prokaryotic expression systems. Peptide subunit vaccines often require adjuvants or conjugates to enhance the immune response.

The SARS-CoV and MERS-CoV outbreak strains in recent years have been extensively studied, and much is known about their structure and the protective neutralizing antibodies induced in recovered patients. These data have been correlated with the nearly daily updated data on the 2019 SARS-CoV-2 coronavirus to predict the protective antigens that can be used in vaccine development for this pathogen, specifically epitopes in the spike (S) protein that interfere with angiotensin-converting enzyme 2 (ACE2) receptor binding to airway epithelial cells. (Jiang S, Hillyer C, Du L. Neutralizing Antibodies against SARS-CoV-2 and Other Human Coronaviruses. Trends in immunology. 2020; 41(5):355-9). There are also reports that inducing a cellular response against the virus is also an important component of preventing disease.

Nucleic acid vaccines, whether viral or non-viral, are safer than the traditional vaccines that require processing of whole pathogens, and simpler to produce than subunit vaccines. Clinical delivery of an antigen-encoding plasmid results in expression directly from the vaccine recipient's tissues. With the choice of the correct antigen, a protective immune response can be induced.

Conversion of a protein therapy to a gene therapy has several potential advantages. Proteins are expressed by transfected host cells over a period of time, so fewer treatments are necessary. This is less toxic, since it is not necessary to deliver a high concentration protein bolus to maintain therapeutic levels. Peptides receive the appropriate posttranslational modifications. Viruses mutate, producing adaptation to human host or even evading the host immune response. In particular, plasmid-based gene therapies can be quickly modified to address these issues.

The inventors develop a dual-mechanism SARS-CoV-2 protein vaccine that does not require extensive plasmid engineering. It is well known that the SARS-CoV-2 spike (S) receptor binding (RGB) domain binds ACE2 in respiratory epithelial cells to initiate infection and SARS-CoV-2 neutralizing antibodies target this region. (Zhou P, et al., A pneumonia outbreak associated with a new coronavirus of probable bat origin. Nature. 2020; 579(7798):270-3. Epub 2020 Feb. 6; Shi R, et al., A human neutralizing antibody targets the receptor binding site of SARS-CoV-2. Nature. 2020. Epub 2020 May 27; Cao Y, et al., Potent neutralizing antibodies against SARS-CoV-2 identified by high throughput single-cell sequencing of convalescent patients' B cells. Cell. 2020. Epub 2020 May 20). The inventors engineer a plasmid encoding the spike protein or its domains, including the RGB domain in frame with a secretion sequence to produce soluble proteins.

The proposed gene therapy works by dual mechanisms, each of which is effective individually. Transfected host cells secrete soluble S peptides which may bind ACE2 on any cell expressing ACE2 to block SARS-CoV-2 binding. In parallel, this peptide acts as an antigen to induce systemic and polyclonal potentially neutralizing antibodies to SARS-CoV-2. In some cases, the S peptides may bind to the antibody, which would result in a dead-end response.

Prophetic Vaccine Administration Example (Spike Protein)

A 64 year old female tests negative for COVID-19. The patient is administered a therapeutically effective amount of a SARS-CoV-2 vaccine that is in the form of a plasmid encoding the SARS-CoV-2 spike protein for a time period sufficient to alleviate symptoms.

Briefly, the plasmid is administered to the patient intradermally or intramuscularly. Moderate heat is applied to the treatment area, once desired temperature is obtained, a low applied voltage is administered to ensure delivery to the tissue. Impedance is measured to establish a preset impedance value. Electroporation is applied to the treatment area to deliver the molecule to the tissue. Impedance is measured as a feedback control mechanism after each pulse to determine permeability of cell membranes. Pulse parameters are adjusted based on the measured impedance until desired impedance is reached indicating delivery of the molecule to the target tissue.

Blood is collected from the patient at baseline (Day 0) and then at regular intervals following administration. Serum is evaluated for levels of anti-SARS-CoV-2 antibodies by ELISA. The female is exposed to COVID-19 through contact with multiple people infected with the virus. The female does not develop a COVID-19 infection as confirmed by testing. Using this delivery approach, a cellular response against the S protein and the virus is stimulated.

Example 8—Administration of SARS-CoV-2 Therapeutic Using Recombinant Soluble Human ACE2 (Prophetic)

Recombinant soluble human ACE2 has been tested in vitro and inhibits SARS-CoV-2 infection. (Monteil V, et al., Inhibition of SARS-CoV-2 Infections in Engineered Human Tissues Using Clinical-Grade Soluble Human ACE2. Cell. 2020; 181(4):905-13 e7). The inventors develop a potential second plasmid to encode a soluble form of the ACE2 receptor consisting of the ACE extracellular domain in frame with a secretion sequence. Since soluble ACE2 is present in the circulation of normal individuals and has been used therapeutically for lung injury, the inventors do not anticipate the formation of anti-ACE2 antibodies. (Ciaglia E, Vecchione C, Puca A A. COVID-19 Infection and Circulating ACE2 Levels: Protective Role in Women and Children. Front Pediatr. 2020; 8:206).

Prophetic Therapeutic Example (ACE2)

A 46 year old female presents with fever, cough, and loss of taste and smell. A diagnosis of COVID-19 is confirmed. The patient is administered a therapeutically effective amount of a SARS-CoV-2 therapeutic that is in the form of a plasmid encoding a soluble form of the ACE2 receptor for a time period sufficient to alleviate symptoms.

Briefly, the plasmid is administered to the patient intradermally or intramuscularly. Moderate heat is applied to the treatment area, once desired temperature is obtained, a low applied voltage is administered to ensure delivery to the tissue. Impedance is measured to establish a preset impedance value. Electroporation is applied to the treatment area to deliver the molecule to the tissue. Impedance is measured as a feedback control mechanism after each pulse to determine permeability of cell membranes. Pulse parameters are adjusted based on the measured impedance until desired impedance is reached indicating delivery of the molecule to the target tissue.

Blood is collected from the patient at baseline (Day 0) and then at regular intervals following treatment. Serum is evaluated for levels of anti-SARS-CoV-2 antibodies by ELISA. The patient is retested twice after completion of treatment over a several week timespan and tests negative for the virus.

Example 9—SARS-CoV-2 Therapeutic Using Nanobodies (Prophetic)

Nanobodies (single domain antibodies) can bind to a single specific antigenic target. The nanobody is comprised of the variable region of the heavy chain of an antibody. (Muyldermans S. Nanobodies: natural single-domain antibodies. Annu Rev Biochem. 2013; 82:775-97; Pardon E, et al., A general protocol for the generation of Nanobodies for structural biology. Nature protocols. 2014; 9(3):674-93). These single-domain antibodies were originally engineered in camelids. They are more resistant to detergents and high concentrations of urea. The small size enables the nanobody to more readily traverse tissues and to be able to bind secluded targets.

Nanobodies that bind specific epitopes of the S protein could inhibit binding of the virus to its target (ACE2). (Walter J D, et al., Sybodies targeting the SARS-CoV-2 receptor-binding domain. bioRxiv. 2020: 2020.04.16.045419). The downside of utilizing the nanobodies as direct protein therapy is the half-life of the protein. High concentrations are injected in multiple injections.

The approach disclosed in this invention is to encode the nanobody into an expression plasmid and deliver it in a manner that produces systemic levels of the nanobodies. Doing this reduces the number of injections and maintains the nanobody levels for a significantly longer period. In addition, multiple nanobodies can be delivered in combination using this approach which could further enhance the therapeutic potential.

Prophetic Therapeutic Example (Nanobodies)

A 35 year old male presents with headache, cough and nausea. A diagnosis of COVID-19 is confirmed. The patient is administered a therapeutically effective amount of a SARS-CoV-2 therapeutic that is in the form of a plasmid encoding a nanobody binding a specific epitope of the spike protein for a time period sufficient to alleviate symptoms.

Briefly, the plasmid is administered to the patient intradermally or intramuscularly. Moderate heat is applied to the treatment area, once desired temperature is obtained, a low applied voltage is administered to ensure delivery to the tissue. Impedance is measured to establish a preset impedance value. Electroporation is applied to the treatment area to deliver the molecule to the tissue. Impedance is measured as a feedback control mechanism after each pulse to determine permeability of cell membranes. Pulse parameters are adjusted based on the measured impedance until desired impedance is reached indicating delivery of the molecule to the target tissue.

Blood is collected from the patient at baseline (Day 0) and then at regular intervals following treatment. Serum is evaluated for levels of anti-SARS-CoV-2 antibodies by ELISA. The patient is retested twice after completion of treatment over a several week timespan and tests negative for the virus.

CONCLUSION

The inventors showed that preheating tissue reduced applied voltage by about 25% (45V to 35V) with no adverse side effects. Preheating also was found to reduce the number of pulses required when using a standard voltage of 45V. The inventors also found that the largest change in impedance due to electroporation was in the low frequency range, less than 4 kHz in murine skin. Other types of tissues, such as human skin, may yield different results. In addition, animals having the highest biological responses, regardless of electric field strength used for electroporation, had final mean impedance values that were reduced by 80% or more in murine skin as compared to pre-pulsed values. Other tissues and skin from other animals, such as humans, may yield different values. These results taken together indicate that preheating tissue prior to delivering electroporation pulses in conjunction with monitoring impedance values after delivery of each pulse and adjusting temperature and/or pulse parameters accordingly, allows for targeted delivery within a tissue.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method of delivering an agent to a biological structure comprising:
injecting the agent into the biological structure;
heating the biological structure to a preset temperature wherein the biological structure is heated by an element that is separate from electrodes used to apply at least one electroporation pulse;
measuring impedance of the biological structure to establish a preset impedance value;
applying the at least one electroporation pulse to deliver the molecule into the biological structure;
measuring the impedance of the biological structure as a feedback control mechanism after each pulse to determine permeability of cell membranes; and
adjusting pulse parameters based on the measured impedance of the biological structure until desired impedance is reached indicating delivery of the molecule to the biological structure;
wherein the agent is a vaccine or therapeutic;
wherein the desired impedance is at least a 10% reduction as compared to the preset impedance value.

2. The method of claim 1, further comprising monitoring temperature of the biological structure.

3. The method of claim 1, wherein the agent is a SARS-CoV-2 vector.

4. The method of claim 1, wherein the preset temperature is at least 35° C.

5. The method of claim 1, wherein the impedance feedback is measured in a frequency range of about 0 Hz to about 4 kHz.

6. The method of claim 1, wherein the pulse parameters are selected from the group consisting of electric field intensity, pulse duration, pulse polarity, time interval between pulses, number of applied pulses, and combinations thereof.

7. The method of claim 6, wherein the electric field intensity is between about 5 V/cm to about 2000 V/cm.

8. The method of claim 6, wherein the pulse duration is between about 1 μs to about 1 second.

9. The method of claim 6, wherein the time interval between pulses is between about 1 μs to about 1 second.

10. A method of determining successful delivery of an agent to a biological structure comprising:
delivering the agent to the biological structure comprising
injecting the agent into the biological structure;
heating the biological structure to a preset temperature wherein the biological structure is heated by an element that is separate from electrodes used to apply at least one electroporation pulse; and
applying the at least one electroporation pulse to deliver the molecule into the biological structure;
measuring the impedance of the biological structure as a feedback control mechanism after the injection of the agent into the biological structure to determine a preset impedance value and after each pulse to determine permeability of cell membranes; and
adjusting pulse parameters based on the measured impedance of the biological structure until desired impedance is reached indicating successful delivery of the molecule to the biological structure;
wherein the desired impedance is at least a 10% reduction as compared to the preset impedance value.

11. The method of claim 10, wherein the agent is a vaccine or therapeutic.

12. The method of claim 11, wherein the vaccine or therapeutic is a SARS-CoV-2 vector.

13. The method of claim 10, wherein the preset temperature is at least 35° C.

14. The method of claim 10, wherein the impedance feedback is measured in a frequency range of about 0 Hz to about 4 kHz.

15. The method of claim 10, wherein the pulse parameters are selected from the group consisting of electric field intensity, pulse duration, pulse polarity, time interval between pulses, number of applied pulses, and combinations thereof.

16. The method of claim 15, wherein the electric field intensity is between about 5 V/cm to about 2000 V/cm.

17. The method of claim 15, wherein the pulse duration is between about 1 μs to about 1 second.

18. The method of claim 15, wherein the time interval between pulses is between about 1 μs to about 1 second.

* * * * *

UNITED STATES PATENT AND TRADEMARK OFFICE
CERTIFICATE OF CORRECTION

PATENT NO. : 11,123,554 B2
APPLICATION NO. : 17/104833
DATED : September 21, 2021
INVENTOR(S) : Richard Heller, Loree C. Heller and Mark Jeffery Jaroszeski It is certified that error appears in the above-identified patent and that said Letters Patent is hereby corrected as shown below:

In the Specification

In Column 1, delete Lines 24 - 30, to be replaced with the corrected Government Support interest statement below:
STATEMENT OF GOVERNMENT INTEREST
This invention was made with government support under EB018956 and EB027497 awarded by the National Institutes of Health. The government has certain rights in the invention.

Signed and Sealed this
Thirteenth Day of February, 2024

Katherine Kelly Vidal
*Director of the United States Patent and Trademark Office*